(12) United States Patent
McKay

(10) Patent No.: US 10,029,031 B2
(45) Date of Patent: *Jul. 24, 2018

(54) BONE VOID FILLER HAVING SUSTAINED THERAPEUTIC AGENT RELEASE

(71) Applicant: Warsaw Orthopedic, Inc., Warsaw, IN (US)

(72) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/924,862

(22) Filed: Oct. 28, 2015

(65) Prior Publication Data
US 2017/0119933 A1 May 4, 2017

(51) Int. Cl.
| | | |
|---|---|---|
| A61L 27/54 | (2006.01) | |
| A61L 31/16 | (2006.01) | |
| A61L 27/56 | (2006.01) | |
| A61L 27/58 | (2006.01) | |
| A61L 31/14 | (2006.01) | |
| A61L 27/24 | (2006.01) | |
| A61L 27/10 | (2006.01) | |
| A61L 17/06 | (2006.01) | |
| A61L 29/16 | (2006.01) | |
| A61L 27/48 | (2006.01) | |

(52) U.S. Cl.
CPC ............... *A61L 27/58* (2013.01); *A61L 27/48* (2013.01); *A61L 27/54* (2013.01); *A61L 27/56* (2013.01); *A61L 2300/406* (2013.01); *A61L 2430/02* (2013.01)

(58) Field of Classification Search
CPC .......... A61L 27/54; A61L 31/16; A61L 27/58; A61L 27/56; A61L 2300/406; A61L 31/146; A61L 2300/602; A61L 27/24; A61L 31/044; A61L 2430/02
See application file for complete search history.

(56) References Cited

U.S. PATENT DOCUMENTS

| | | | |
|---|---|---|---|
| 4,837,285 A | 6/1989 | Berg et al. | |
| 4,882,149 A | 11/1989 | Spector | |
| 4,994,388 A | 2/1991 | Hillegas et al. | |
| 5,073,373 A | 12/1991 | O'Leary et al. | |
| 5,417,975 A | 5/1995 | Lussi et al. | |
| 5,573,771 A | 11/1996 | Geistlich et al. | |
| 5,641,514 A * | 6/1997 | Cho ..................... A61K 9/0024 424/487 |
| 5,676,146 A | 10/1997 | Scarborough | |
| 2002/0006427 A1 | 1/2002 | Umezu et al. | |
| 2004/0131681 A1 * | 7/2004 | Ambrose ............. A61K 9/0019 424/469 |
| 2004/0132859 A1 * | 7/2004 | Puckett, Jr. ............. A61L 24/06 523/118 |
| 2005/0085922 A1 * | 4/2005 | Shappley .................. A61F 2/28 623/23.5 |
| 2005/0234114 A1 * | 10/2005 | Lee ....................... A61K 9/0048 514/365 |
| 2006/0100138 A1 * | 5/2006 | Olsen ....................... A61K 6/08 514/16.5 |
| 2007/0048382 A1 * | 3/2007 | Meyer .................... A61K 31/66 424/487 |
| 2008/0107744 A1 * | 5/2008 | Chu ...................... A61F 2/0036 424/489 |
| 2008/0147197 A1 * | 6/2008 | McKay ................. A61F 2/2846 623/23.51 |
| 2009/0130173 A1 | 5/2009 | Behnam et al. | |
| 2009/0157087 A1 | 6/2009 | Wei et al. | |
| 2009/0264554 A1 * | 10/2009 | Meyer ................... A61L 24/001 523/116 |
| 2010/0203155 A1 | 8/2010 | Wei et al. | |
| 2011/0054408 A1 | 3/2011 | Wei et al. | |
| 2011/0070312 A1 | 3/2011 | Wei et al. | |
| 2012/0009230 A1 * | 1/2012 | Drapeau .................. A61L 27/20 424/400 |
| 2012/0041444 A1 | 2/2012 | Einhorn | |
| 2012/0107383 A1 * | 5/2012 | McKay ................. A61K 9/0024 424/423 |
| 2012/0310366 A1 * | 12/2012 | Li .......................... A61K 31/22 623/23.57 |
| 2013/0280303 A1 * | 10/2013 | Drapeau .............. A61K 31/722 424/400 |
| 2014/0142025 A1 * | 5/2014 | Koob ............... A61K 47/48246 514/2.3 |
| 2014/0294913 A1 | 10/2014 | Hasirci et al. | |

FOREIGN PATENT DOCUMENTS

| | | | | |
|---|---|---|---|---|
| WO | WO 9301841 A1 * | 2/1993 | ........... A61K 9/1635 |
| WO | WO-2014020610 A1 * | 2/2014 | ............. A61L 27/54 |
| WO | WO 2014168565 A1 * | 10/2014 | ............. A61L 27/16 |
| WO | WO-2015135822 A1 * | 9/2015 | ............. A61L 27/12 |

OTHER PUBLICATIONS

International Search Report and Written Opinion for PCT/US2016/058582, the counterpart application dated Feb. 3, 2017, 10 pages.

* cited by examiner

*Primary Examiner* — Tracy Liu

(57) ABSTRACT

A bone void filler material is provided that is configured for sustained release of a therapeutic agent. The bone void filler material comprises a biodegradable matrix having ceramic particles and cement beads disposed within the matrix, the cement beads loaded with the therapeutic agent to cause sustained release of the therapeutic agent. Methods of use are also disclosed.

18 Claims, 4 Drawing Sheets

BONE VOID FILLER HAVING SUSTAINED THERAPEUTIC AGENT RELEASE

BACKGROUND

Bone defects may be caused by a number of different factors, including but not limited to trauma, pathological disease or surgical intervention. Because bone provides both stability and protection to an organism, these defects can be problematic. In order to address these defects, compositions that contain both natural and synthetic materials have been developed. These compositions may, depending upon the materials contained within them, be used to repair tissues and to impart desirable biological and/or mechanical properties.

Among the known bone repair materials and bone void fillers is autologous cancellous bone. This type of bone has the advantage of being both osteoinductive and non-immunogenic. Unfortunately, this type of bone is not available under all circumstances. Moreover, donor site morbidity and trauma add to the limitations of autologous cancellous bone. One alternative to autologous bone is allograft bone. Unfortunately, allograft bone has a lower osteogenic capacity than autograft bone, has a high resorption rate, creates less revascularization at the bone defect site, typically induces a greater immunogenic response and may result in the transfer of certain diseases.

In order to avoid the issues that attach to the use of autologous and allograft bone, one may use synthetic materials. However, known synthetic materials suffer from one or more of the following drawbacks, including unacceptable workability, handling and setting parameters; insufficient density; undesirable absorption rates; and an inability to impart adequate stability.

Another issue arises when therapeutic agents are added to the bone repair materials and bone void fillers. Currently, ceramic settable cements exist that trap therapeutics agents within them and then the therapeutic agents are released as the ceramic resorbs. These settable cements do not make good bone grafting materials due to their lack of porosity.

Accordingly, there is a need for new defect fillers that have a therapeutic agent, such as an antibiotic, released from highly porous bone void fillers as the new bone grows within the bone void filler matrix.

SUMMARY

The bone void filler material provided, unlike typical bone cements loaded with a therapeutic agent (e.g., antibiotic), are porous to allow controlled release of the therapeutic agent. In some embodiments, there is a bone void filler material comprising a biodegradable matrix having ceramic particles and cement beads disposed within the matrix. The cement beads are loaded with the therapeutic agent to cause sustained release of the therapeutic agent.

In some embodiments, a bone void filler material for sustained release of a therapeutic agent is provided. The bone void filler material comprising a biodegradable matrix having collagen particles and ceramic particles disposed within the matrix, the collagen particles are admixed with the therapeutic agent and cross-linked to cause sustained release of the therapeutic agent.

In various embodiments, a bone void filler material for sustained release of a therapeutic agent is provided. The bone void filler material comprising a biodegradable matrix having ceramic particles. The ceramic particles are loaded with the therapeutic agent and coated with cross-linked collagen to cause sustained release of the therapeutic agent.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1:
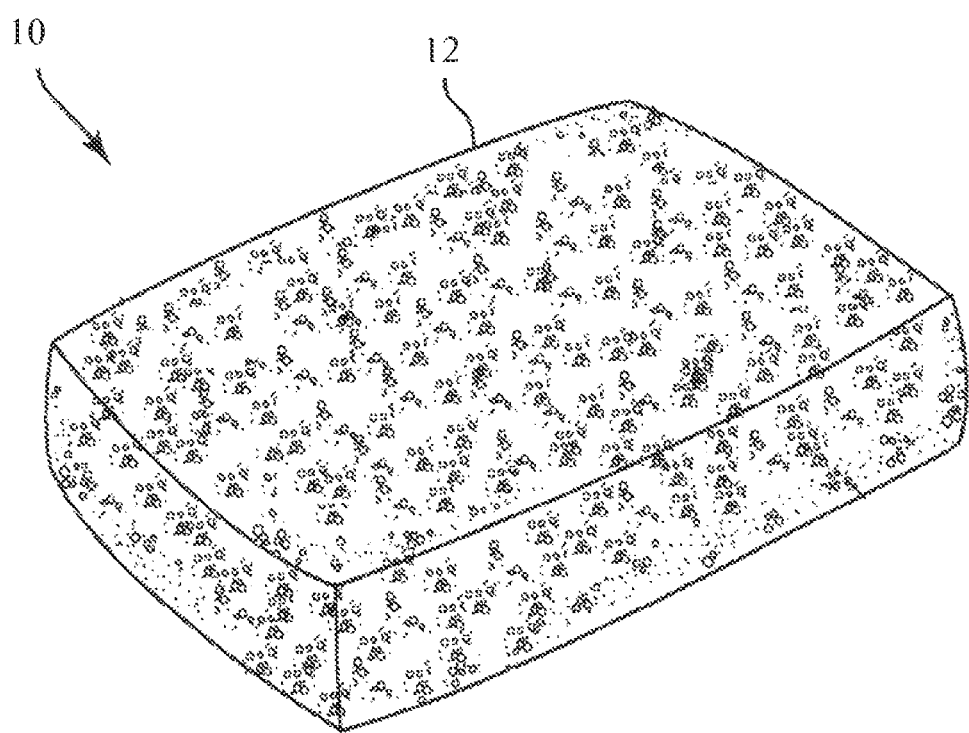
FIG. 1 depicts a bone void filler configured for sustained release of a therapeutic agent. In various embodiments, the bone void filler material comprises a collagen sponge matrix, cement beads and/or various configurations of collagen particles and/or ceramic particles disposed within the collagen sponge matrix.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of promoting an understanding of the principles of the disclosure, reference will now be made to certain embodiments and specific language will be used to describe the same. It will nevertheless be understood that no limitation of the scope of the disclosure is thereby intended, such alterations and further modifications in the illustrated device, and such further applications of the principles of the disclosure as described herein being contemplated as would normally occur to one skilled in the art to which the disclosure relates.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical representations are as precise as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Additionally, unless defined otherwise or apparent from context, all technical and scientific terms used herein have the same meanings as commonly understood by one of ordinary skill in the art to which this disclosure belongs.

Unless explicitly stated or apparent from context, the following terms are phrases have the definitions provided below:

Definitions

It is noted that, as used in this specification and the appended claims, the singular forms "a," "an," and "the," include plural referents unless expressly and unequivocally limited to one referent. Thus, for example, reference to "a matrix" includes one, two, three or more matrices.

The term "biodegradable" includes that all or parts of the bone void filler, sponge matrix, beads and/or particles that will degrade over time by the action of enzymes, by hydrolytic action and/or by other similar mechanisms in the human body. In various embodiments, "biodegradable" includes that the bone void filler, sponge matrix, beads and/or particles can break down or degrade within the body to non-toxic components after or while a therapeutic agent has been or is being released. By "bioerodible" it is meant that the bone void filler, sponge matrix, beads and/or particles will erode or degrade over time due, at least in part, to contact with substances found in the surrounding tissue, fluids or by cellular action.

The term "mammal" refers to organisms from the taxonomy class "mammalian," including but not limited to humans, other primates such as chimpanzees, apes, orangutans and monkeys, rats, mice, cats, dogs, cows, horses, etc.

A "therapeutically effective amount" or "effective amount" is such that when administered, the therapeutic agent/drug results in alteration of the biological activity, such as, for example, promotion of bone, cartilage and/or other tissue (e.g., vascular tissue) growth, inhibition of inflammation, reduction or alleviation of pain, improvement in the condition through inhibition of an immunologic response, etc. The dosage administered to a patient can be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments the bone void filler, sponge matrix, beads and/or particles is designed for immediate release. In other embodiments the bone void filler, sponge matrix, beads and/or particles is designed for sustained release. In other embodiments, the bone void filler, sponge matrix, beads and/or particles comprises one or more immediate release surfaces and one or more sustained release surfaces.

The terms "sustained release" and "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period. Reference to a continuous or continual release stream is intended to encompass release that occurs as the result of biodegradation in vivo of the drug depot, or a fiber or component thereof, or as the result of metabolic transformation or dissolution of the therapeutic agent(s) or conjugates of therapeutic agent (s).

The two types of formulations (sustain release and immediate release) may be used in conjunction. The sustained release and immediate release may be in one or more of the same bone void filler, sponge matrix, beads and/or particles. In various embodiments, the sustained release and immediate release may be part of separate sponge matrices. For example a bolus or immediate release formulation may be placed at or near the target site and a sustain release formulation may also be placed at or near the same site. Thus, even after the bolus becomes completely accessible, the sustain release formulation would continue to provide the active ingredient for the intended tissue.

The phrase "release rate profile" refers to the percentage of therapeutic agent/active ingredient that is released over fixed units of time, for example, mcg/hr, mcg/day, 10% per day for ten days, etc. As persons of ordinary skill know, a release rate profile may, but need not, be linear. By way of a non-limiting example, the bone void filler may be a collagen sponge matrix comprising ceramic cement beads loaded with a therapeutic agent that releases the therapeutic agent over a period of time.

The terms "treating" and "treatment" when used in connection with a disease or condition refer to executing a protocol that may include a bone repair procedure, where the bone void filler and/or one or more drugs are administered to a patient (human, other normal or otherwise or other mammal), in an effort to alleviate signs or symptoms of the disease or condition or immunological response. Alleviation can occur prior to signs or symptoms of the disease or condition appearing, as well as after their appearance. Thus, treating or treatment includes preventing or prevention of disease or undesirable condition. In addition, treating, treatment, preventing or prevention do not require complete alleviation of signs or symptoms, does not require a cure, and specifically includes protocols that have only a marginal effect on the patient.

The term "bone," as used herein, refers to bone that is conical, cancellous or cortico-cancellous of autogenous, allogenic, xenogenic, or transgenic origin.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "osteoconductive," as used herein, refers to the ability of a non-osteoinductive substance to serve as a suitable template or substance along which bone may grow.

"Non-allograft bone material" refers to implantable material that is not obtained from allograft bone. Non-allograft bone material can be synthetic material (e.g., ceramic, synthetic polymers, etc.) or non-synthetic non-bone material (e.g., collagen, chitosan, alginate, elastic, etc.). The non-allograft bone material is made into fibers to mimic the allograft bone fibers. The non-allograft bone material can then be made osteogenic, osteoinductive, and/or osteoconductive by, embedding or adding DBM material to the non-allograft bone fibers. This includes DBM in the form of fragments, slices, pellets, shavings, granules, fibers, or powder or the like, which can be coated on, attached to, or embedded in the non-allograft bone fibers.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "particles" as utilized herein is intended to include relatively small pieces such as fibers, bundles of loosely connected fibers, threads, narrow strips, thin sheets, beads, chips, shards, powders, depots, etc, that possess regular, irregular or random geometries and which may, or may not, be completely separated from each other.

The term "demineralized," as used herein, refers to any material generated by removing mineral material from tissue, e.g., bone tissue. In certain embodiments, demineralized bone material may be added to the bone void filler. The demineralized bone material described herein include preparations containing less than 5%, 4%, 3%, 2% or 1% calcium by weight. Partially demineralized bone (e.g., preparations with greater than 5% calcium by weight but containing less than 100% of the original starting amount of calcium) is also considered within the scope of the disclosure. In some embodiments, partially demineralized bone contains preparations with greater than 5%, 10%, 15%, 20%, 25%, 30%, 35%, 40%, 45%, 50%, 55%, 60%, 65%, 70%, 75%, 80%, 85%, 90%, 95%, 96%, 97%, 98% or 99% of the original starting amount of calcium. In some embodiments, demineralized bone has less than 95% of its original mineral content. In some embodiments, demineralized bone has less than 95%, 90%, 85%, 80%, 75%, 70%, 65%, 60%, 55%, 50%, 45%, 40%, 35%, 30%, 25%, 20%, 15%, 10%, or 5% of its original mineral content. Demineralized is intended to encompass such expressions as "substantially demineralized," "partially demineralized," and "fully demineralized." In some embodiments, part or all of the surface of the bone can be demineralized. For example, part or all of the surface of the bone material can be demineralized to a depth of from about 100 to about 5000 microns, or about 150 microns to about 1000 microns. In some embodiments, part or all of the surface of the bone material can be demineralized to a depth of from about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3050, 3100, 3150, 3200, 3250, 3300, 3350, 3400, 3450, 3500, 3550, 3600, 3650, 3700, 3750, 3800, 3850, 3900, 3950, 4000, 4050, 4100, 4150, 4200, 4250, 4300, 4350, 4400, 4450, 4500, 4550, 4600, 4650, 4700, 4750, 4800, 4850, 4900, 4950 to about 5000 microns. If desired, the bone void filler can comprise demineralized material.

The term "demineralized bone matrix," as used herein, refers to any material generated by removing mineral material from bone tissue. In some embodiments, the DBM compositions as used herein include preparations containing less than 5%, 4%, 3%, 2% or 1% calcium by weight.

The term "superficially demineralized," as used herein, refers to bone-derived elements possessing at least about 90, 91, 92, 93, 94, 95, 96, 97, 98 or 99 weight percent of their original inorganic mineral content. The expression "partially demineralized" as used herein refers to bone-derived elements possessing from about 8 to about 90 weight percent of their original inorganic mineral content. In some embodiments, partially demineralized refers to bone-derived elements possessing from about 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88 to about 90 weight percent of their original inorganic mineral content. The expression "fully demineralized" as used herein refers to bone containing less than 8%, 7%, 6%, 5%, 4%, 1%, 2%, 1% of its original mineral context.

The terms "pulverized bone", "powdered bone" or "bone powder" as used herein, refers to bone particles of a wide range of average particle size ranging from relatively fine powders to coarse grains and even larger chips.

The bone void filler can comprise bone fibers. Fibers include bone elements whose average length to average thickness ratio or aspect ratio of the fiber is from about 50:11 to about 1000:1. In overall appearance the fibrous bone elements can be described as elongated bone fibers, threads, narrow strips, or thin sheets. Often, where thin sheets are produced, their edges tend to curl up toward each other. The fibrous bone elements can be substantially linear in appearance or they can be coiled to resemble springs. In some embodiments, the elongated bone fibers are of irregular shapes including, for example, linear, serpentine or curved shapes. The elongated bone fibers are preferably demineralized, however, some of the original mineral content may be retained when desirable for a particular embodiment.

"Non-fibrous", as used herein, refers to elements that have an average width substantially smaller than the average thickness of the fibrous bone element or aspect ratio of less than from about 50:1 to about 1000:1. In some embodiments, the non-fibrous bone elements are shaped in a substantially regular manner or specific configuration, for example, triangular prism, sphere, cube, cylinder and other regular shapes. By contrast, particles such as chips, shards, or powders possess irregular or random geometries. It should be understood that some variation in dimension will occur in the production of the elements of this application and elements demonstrating such variability in dimension are within the scope of this application and are intended to be understood herein as being within the boundaries established by the expressions "mostly irregular" and "mostly regular". For example, allograft bone fibers will have a fiber shape, while the non-fibrous material will not have a fiber shape but will have a shape such as, for example, triangular prism, sphere, cube, cylinder, square, particle, and other regular or irregular shapes. The non-fibrous material can be material obtained after the fiber has been harvested from the allograft bone. In some embodiments, the non-fibrous, non-allograft material is synthetic and not obtained from allograft bone.

"Pressed bone fibers", as used herein, refer to bone fibers formed by applying pressure to bone stock. The bone utilized as the starting, or stock, material may range in size from relatively small pieces of bone to bone of such dimensions as to be recognizable as to its anatomical origin. The bone may be substantially fully demineralized, surface demineralized, partially demineralized, or nondemineralized. Forming bone fibers by pressing results in intact bone fibers of longer length than other methods of producing the elongate bone fibers retaining more of the native collagen structure. The bone may be particulated via pressure applied to the bone, as discussed in U.S. Pat. No. 7,323,193, herein incorporated by reference.

"High porosity", as used herein refers to having a pore structure that is conducive to cell ingrowth, and the ability to promote cell adhesion, proliferation and differentiation.

"Resorbable", as used herein, refers to a material that exhibits chemical dissolution when placed in a mammalian body.

"Admix" or "Admixed", as described herein, refers to the blending or mixing of two or more compounds.

"Adsorb" or "adsorbtion", as described herein, refers to the adhesion of atoms, ions, or molecules from a gas, liquid, or dissolved solid to a surface. This process creates a film of the adsorbate (e.g., therapeutic agent) on the surface of the adsorbent.

"Therapeutic agent", "Bioactive agent", or "bioactive compound", as used herein, refers to a compound or entity that alters, inhibits, activates, or otherwise affects biological or chemical events. For example, therapeutic agents/bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In some embodiments, the therapeutic agent/bioactive agent is a growth factor, cytokine, extracellular matrix molecule or a fragment or derivative thereof, for example, a cell attachment sequence such as RGD.

Reference will now be made in detail to certain embodiments of the disclosure. The disclosure is intended to cover all alternatives, modifications, and equivalents that may be included within the disclosure as defined by the appended claims.

The headings below are not meant to limit the disclosure in any way; embodiments under any one heading may be used in conjunction with embodiments under any other heading.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

Matrix

The bone void filler comprises a sponge matrix. In some embodiments, the sponge matrix is collagen. Collagen has excellent histocompatibility without antibody formation or graft rejection. Any suitable collagen material may be used, including known collagen materials, or collagen materials as disclosed in U.S. patent application Ser. No. 12/030,181, Filed Feb. 12, 2008, hereby incorporated by reference in its entirety. Various collagen materials can be used, alone or in combination with other materials.

In some embodiments, insoluble collagen can be used and can be derived from natural tissue sources, (e.g. xenogeneic, allogenic, or autogenic relative to the recipient human or other patient) or recombinantly prepared. Collagens can be subclassified into several different types depending upon their amino acid sequence, carbohydrate content and the presence or absence of disulfide crosslinks. Types I and III collagen are two of the most common subtypes of collagen and may be used in the present disclosure. Type I collagen is present in skin, tendon and bone, whereas Type III collagen is found primarily in skin. The collagen can be obtained from skin, bone, tendon, or cartilage and purified by methods well known in the art and industry. Alternatively, the collagen can be purchased from commercial sources.

The collagen can be atelopeptide collagen and/or telopeptide collagen. Still further, either or both of non-fibrillar and fibrillar collagen can be used. Non-fibrillar collagen is collagen that has been solubilized and has not been reconstituted into its native fibrillar form.

Suitable collagen products are available commercially, including for example from Kensey Nash Corporation (Exton, Pa.), which manufactures a fibrous collagen known as Semed F, from bovine hides. Collagen materials derived from bovine hide are also manufactured by Integra Life Science Holding Corporation (Plainsboro, N.J.). Naturally-derived or recombinant human collagen materials are also suitable for the sponge matrix. Illustratively, recombinant human collagen products are available from Fibrogen, Inc. (San Francisco, Calif.).

In various embodiments, solid particulate collagen can be incorporated into the sponge matrix in the form of intact or reconstituted fibers, or randomly-shaped particles, for example. In some embodiments, the solid particulate collagen will be in the form of particles derived from a separate sponge material, for example by randomly fragmenting the sponge material by milling, shredding or other similar operations. Such particulated sponge material can have an average maximum particle diameter of less than about 6 mm, more preferably less than about 3 mm, and advantageously in the range of about 0.5 mm to 2 mm. Such materials can, for example, be obtained by milling or grinding a porous sponge material and sieving the milled or ground material through a screen having openings sized about 6 mm or smaller, desirably about 0.5 mm to about 2 mm. Retch grinders with associated sieves are suitable for these purposes. Other sources of chemically crosslinked, particulate collagen, in fiber, irregular or other shapes, can be incorporated into the sponge matrix. Crosslinked solid collagen particles can be used in combination with non-crosslinked collagen in the sponge matrix, where the non-crosslinked collagen can be solid (insoluble) or soluble collagen, or combinations thereof. Such crosslinked and non-crosslinked collagen mixtures can be used, for example, to modulate the residence time of the collagen sponge matrix in vivo.

Suitable crosslinking agents include, but are not limited to, mono- and dialdehydes, including glutaraldehyde and formaldehyde; polyepoxy compounds such as glycerol; sugars such as glucose. In one embodiment, the crosslinking agent is glycerol.

Exemplary collagen particles employed for the sponge matrix can be obtained from various collagen sources including human or non-human (bovine, ovine, and/or porcine), as well as recombinant collagen or combinations thereof. Examples of suitable collagen include, but are not limited to, human collagen type I, human collagen type II, human collagen type HI, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homotrimers of any of the above-recited collagen types. In some embodiments, the collagen comprises hetero- or homo-trimers of human collagen type I, human collagen type II, human collagen type HI, or combinations thereof. In some embodiments, the collagen is porous.

In some embodiments, the sponge matrix comprises 100% weight percent of collagen. In some embodiments, the sponge matrix comprises from about 1 to about 100%, from about 10 to about 90%, from about 20 to about 80%, from about 30 to about 70%, from about 40 to about 60%, from about 50 to 55%, from about 1 to about 15, from about 15 to about 30, from about 30 to about 50, from about 50 to about 70, or from about 70 to about 90% weight percent of collagen. In some embodiments, the sponge matrix comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% weight percent of collagen.

In some embodiments, the sponge matrix alternatively comprises a material comprising hyaluronic acid, chitosan, chitin, keratin, alginate, cellulose, glycosaminoglycans and derivatives thereof (e.g. esters of hyaluronic acid) or materials of synthetic origin which may be used as an alternative to or in combination with the collagen. In various embodiments, the sponge matrix comprises a ratio of collagen to hyaluronic acid, chitosan, chitin, keratin, alginate, cellulose, glycosaminoglycans and derivatives thereof (e.g. esters of hyaluronic acid) or materials of synthetic origin of about 10:1, 9:1, 8:1, 7:1, 6:1, 5:1, 4:1, 3:1, 2:1, 1:1, 1:10, 1:9, 1:8, 1:7, 1:6, 1:5, 1:4, 1:3, or 1:2. In various embodiments, the sponge matrix comprises a material comprising hyaluronic acid, chitosan, chitin, keratin, alginate, cellulose, glycosaminoglycans and derivatives thereof (e.g. esters of hyaluronic acid) or materials of synthetic origin at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% weight percent. In some embodiments, the sponge matrix comprises 100% weight percent of one of the materials described directly above. In some embodiments, the sponge matrix comprises from about 1 to about 100%, from about 10 to about 90%, from about 20 to about 80%, from about 30 to about 70%, from about 40 to about 60%, from about 50 to 55%, from about 1 to about 15, from about 15 to about 30, from about 30 to about 50, from about 50 to about 70, or from about 70 to about 90% weight percent of one of the materials described directly above.

In some embodiments, it may also be possible to include additional polymers (e.g., natural or synthetic biodegradable polymers) in the sponge matrix to give the matrix a degree of enhanced ductility. Additional polymers include, but are not limited to hydrophobic polymers (e.g. poly(lactide-co-glycolyde), poly-anhydrides). Alternatively, a combination of hydrophilic and hydrophobic polymers may be used. Additionally, biopolymers and synthetic polymers such as human skin, human hair, bone, collagen, fat, thin cross-linked sheets containing fibers and/or fibers and chips, polyethylene glycol (PEG), chitosan, alginate sheets, cellulose sheets, hyaluronic acid sheets, as well as copolymer blends of poly-lactic polyglycolic acid copolymers (PLGA) can be used. In some embodiments, the sponge matrix can also include other biocompatible and bioresorbable substances. These materials may include, for example, natural polymers such as proteins and polypeptides, glycosaminoglycans, proteoglycans, elastin, hyaluronic acid, derinatan sulfate, gelatin, or mixtures or composites thereof. Synthetic polymers such as, biodegradable synthetic polymers of polylactic acid, polyglycolide, polycaprolactone (PCL), poly(dioxanone), poly(trimethylene carbonate) copolymers, polyglyconate, polypropylene fumarate), poly(ethylene terephthalate), polybutylene terephthalate), polyethylene glycol, polycaprolactone copolymers, polyhydroxybutyrate, polyhydroxyvalerate, tyrosine-derived polycarbonates and any random or (multi-)block copolymers, such as bipolymer, terpolymer, quaterpolymer, etc., that can be polymerized from the monomers related to previously-listed homo- and copolymers can be used.

The polymers described above may have a molecular weight of from about 1,000 to about 30,000 Daltons (Da) In various embodiments, the polymer may have a molecular weight of from about 2,000 to about 10,000 Da. In some embodiments, the polymer may have a molecular weight of from about 2,000 to 4,000 Da or from about 3,000 to 4,000 Da. In some embodiments, the bioerodible polymer may have a molecular weight of 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000 Da.

The sponge matrix is porous. In some embodiments, the sponge matrix has a porosity of 1, 2, 3, 4, 5, 6, 7, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. The sponge matrix comprises pores. In some embodiments, the pore sizes of the sponge matrix are about 1 to about 1,000 microns, about 1 to about 200 microns, about 200 to about 400 microns, about 400 to about 600 microns, about 600 to about 800 microns or about 800 to about 1,000 microns. In various embodiments, the pore size of the pores is about 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 and/or 1000 microns. In some embodiments, the pore sizes are the same size and uniformly distributed throughout the sponge matrix.

In some embodiments, the pore sizes vary and range from about 1 to about 1,000 microns, in various embodiments, about 90% of the pores are from 1 to about 500 microns and about 10% of the pores are from about 500 to 1,000 microns, about 80% of the pores are from 1 to about 500 microns and about 20% of the pores are from about 500 to 1,000 microns, about 70% of the pores are from 1 to about 500 microns and about 30% of the pores are from about 500 to 1,000 microns, about 60% of the pores are from 1 to about 500 microns and about 40% of the pores are from about 500 to 1,000 microns, about 50% of the pores are from 1 to about 500 microns and about 50% of the pores are from about 500 to 1,000 microns, about 40% of the pores are from 1 to about 500 microns and about 60% of the pores are from about 500 to 1,000 microns, about 30% of the pores are from 1 to about 500 microns and about 70% of the pores are from about 500 to 1,000 microns, about 20% of the pores are from 1 to about 500 microns and about 80% of the pores are from about 500 to 1,000 microns and about 10% of the pores are from 1 to about 500 microns and about 90% of the pores are from about 500 to 1,000 microns.

In various embodiments, the sponge matrix has an average molecular weight from about 1,000 to about 10,000,000 Da, about 1,000 to about 1,000,000 Da, about 5,000 Da to about 500,000 Da, about 10,000 Da to about 100,000 Da, or about 20,000 Da to 50,000 Da. In some embodiments, 1,000, 2,000, 3,000, 4,000, 5,000, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000 or about 30,000, 40,000, 50,000, 60,000, 70,000, 80,000, 90,000, 100,000, 120,000, 140,000, 160,000, 180,000, 200,000, 220,000, 240,000, 260,000, 280,000, 300,000, 320,000, 340,000, 360,000, 380,000, 400,000, 420,000, 440,000, 460,000, 480,000, 500,000, 520,000, 540,000, 560,000, 580,000, 600,000, 620,000, 640,000, 660,000, 680,000, 700,000, 720,000, 740,000, 760,000, 780,000, 800,000, 820,000, 840,000, 860,000, 880,000, 900,000, 920,000, 940,000, 960,000, 980,000, 1,000,000, 2,000,000, 3,000,000, 4,000,000, 5,000,000, 6,000,000, 7,000,000, 8,000,000, 9,000,000, or 10,000,000 Da.

In various embodiments, the sponge matrix has a modulus of elasticity in the range of about $1\times10^2$ to about $6\times10^5$ dyn/cm$^2$, or $2\times10^4$ to about $5\times10^5$ dyn/cm$^2$, or $5\times10^4$ to about $5\times10^5$ dyn/cm$^2$. In some embodiments, the sponge matrix has a modulus of elasticity in the range of about $1\times10^2$ to about $6\times1.0^5$ dynes/cm$^2$, or $2\times10^4$ to about $5\times10^5$ dynes/cm$^2$, or $5\times10^4$ to about $5\times10^5$ dynes/cm$^2$.

Cement Beads

Typically, bone cement compositions comprise a two-part preparations containing a powder (or dry) part (e.g., polymethylmethacrylate) often in beads and a liquid (or wet) part, which, when combined, polymerize to form a hardened substance mimicking many of the physical properties of natural bone. The powder part includes a filler and a polymeric material (e.g., PMMA beads loaded, impregnated, or coated with the therapeutic agent (e.g., antibiotic)), while the liquid part includes a reactive monomer (e.g., methylmethacrylate). The filler is a material that is bioactive on its surface to promote the natural growth of bone thereon. An example of such a filler is hydroxyapatite. Hydroxyapatite has a large surface area that undesirably absorbs the reactive monomer. There is typically an excess amount of reactive monomer because a portion of the reactive monomer is absorbed into the hydroxyapatite and, therefore, does not participate in the polymerization reaction. When the two parts are combined there is a polymerization reaction to form the bone cement, which changes over time from a runny liquid into a dough like state that can be safely applied and then finally hardens into solid hardened material. The set time can be tailored to help the physician safely apply the bone cement to the bone cavity. "Settable bone cements" include compositions that are in a form that permits a practitioner to implant the cement through, e.g., a syringe. After being implanted, the cement can set e.g., harden where it is deposited or be manipulated into a desired shape and then deposited prior to hardening. A non-limiting example of settable cement is Bone Solutions OsteoCrete™. However, the cement beads in the present application are coated, impregnated, or loaded with the therapeutic agent (e.g., antibiotic). These beads are incorporated into a biodegradable matrix (e.g., collagen, chitosan, keratin, alginate, hyaluronic acid, etc.) homogenously or in layers with ceramic particles. The porous matrix allows bodily fluids to pass into the porous matrix and the fluid contacts the cement beads and the therapeutic agent (e.g., antibiotic) is released from the matrix to inhibit microbial growth in the matrix and at or near the implant site.

In some embodiments, the first component of the cement beads generally includes about 0.5 wt. % to about 99.5 wt. % of the spray-dried inorganic filler, based on the total weight of the first component. In some embodiments, the first component includes about 10 wt. % to about 70 wt. % of the filler, or about 30 wt. % to about 50 wt. % of the filler, based on the total weight of the first component.

As noted above, the first component, in some embodiments, can include a pre-polymerized vinyl polymer. The pre-polymerized vinyl polymer can comprise poly(methyl methacrylate) (PMMA), prepolymerized styrene acrylates, poly-methacrylate, polyethacrylate, poly-butylmethacrylate, and copolymers thereof, and mixtures thereof. As noted above, the pre-polymerized vinyl polymer can comprise beads having an average particle size of about 20 micrometers to about 35 micrometers. In some embodiments, the pre-polymerized vinyl polymer comprises PMMA.

In some embodiments, the first component includes about 0.5 wt. % to about 99.5 wt. % of the pre-polymerized vinyl polymer, based on the total weight of the first component. In some embodiments, the first component includes about 50 wt. % to about 90 wt. % of the pre-polymerized vinyl polymer, or about 30 wt. % to about 70 wt. % of the pre-polymerized vinyl polymer, based on the total weight of the first component.

A radical donor can also be present in the first component. The radical donor is used to initiate a polymerization reaction with the reactive monomer present in the second component. The radical donor can be benzoyl peroxide (BPO), azo-bis-isobutyrylnitrite (AIBN), and mixtures thereof. In one embodiment, the balance of the first component generally is made up of the radical donor. Thus, the first component can include about 0.5 wt. % to about 5 wt. % of the radical donor, based on the total weight of the inorganic filler and the pre-polymerized vinyl polymer. In some embodiments, the first component includes about 0.6 wt. % to about 3 wt. % of the radical donor, and even more preferably about 0.9 wt. % to about 2 wt. % of the radical donor, based on the total weight of the spray-dried inorganic filler and the pre-polymerized vinyl polymer.

In one embodiment, the second component can include a polymerization accelerator, a reactive monomer, a diluent, and a radical scavenger. The polymerization accelerator is selected such that the polymerization reaction occurs at or below normal body temperatures so as not to cause damage to the surgical site and surrounding areas. The polymerization accelerator can be a tertiary amine. Suitable tertiary amines include, but are not limited to, dimethylparatoluidine (DMPT) and dihydroxyethylorthotoluidine. Although, DMPT is believed to be toxic to humans, in low concentrations, it may still be used without adverse consequences. The second component can include about 0.1 wt. % to about 3 wt. % of the polymerization accelerator, based on the total weight of second component. The second component can include about 0.2 wt. % to about 2 wt. % of the polymerization accelerator or about 0.3 wt. % to about 0.4 wt. % of the polymerization accelerator, based on the total weight of the second component.

A reactive monomer also is present in the second component. The reactive monomer can be methyl methacrylate (MMA), PEG monoactylates, PEG diacrylates, PEG monomethactylates, PEG dimethacrylates, PEG-mono/di-acrylate/methacrylate, butanediol methacrylates, polyolefin-acrylates, urethaneacrylates, methacrylates, or mixtures thereof. Among the PEG-based reactive monomers, those having a molecular weight in a range of about 200 Daltons (D) to about 1500 D are preferred. In some embodiments, the reactive monomer comprises MMA.

The second component can include about 10 wt. % to about 99 wt. % of the reactive monomer, based on the total weight of the second component. In some embodiments, the second component includes about 40 wt. % to about 95 wt. % of the reactive monomer or about 60 wt. % to about 90 wt. % of the reactive monomer, based on the total weight of the second component.

In one embodiment, the second component can also include a diluent. Suitable diluents include, but are not limited to, polyethylene glycol (PEG), an ester of mellitic acid, and mixtures thereof. Preferably, the diluent is PEG. When present, a preferred ester of mellitic acid is tri-octylmellitic ester. Generally, the diluent should have a molecular weight such that the diluent remains in liquid form at room temperature. When PEG is used, preferably its molecular weight is about 100 D to about 1000 D, and more preferably about 400 D to about 800 D. The presence of the diluent in the second component provides multiple benefits. For example, the diluent desirably provides the ability to control the stiffness of the bone cement composition after curing/hardening. While not wishing to be bound by any particular theory, it is believed that lower stiffness is beneficial because it better simulates the actual properties of human bones. The presence of PEG in the aforementioned weight range does not adversely affect the compressive strength and bending strength of the preparation. Thus, the stiffness can be more readily/easily controlled by the presence of PEG, without compromising the compressive and bending strengths of the preparation relative to the prior art preparations. The compressive and bending strengths may be adversely affected when the amount of diluent exceeds 30 wt. %, based on the total weight of the composition. Furthermore, the presence of diluent rapidly destabilizes the radical donor (thus, resulting in a faster hardening of the preparation) and reduces the amount of polymerization accelerator (e.g., DMPT) necessary. If the compression strength of the hardened preparation can be lowered from 30 mega-Pascal's (mPa), then the amount of diluent (e.g., PEG) can be increased with a concomitant decrease in the amount of reactive monomer.

The second component generally includes about 1 wt. % to about 90 wt. % of the diluent, based on the total weight of the second component. Preferably, the second component includes about 5 wt. % to about 60 wt. % of the diluent, and even more preferably about 10 wt. % to about 40 wt. % of the diluent, based on the total weight of the second component.

In one embodiment, the second component can also include a radical scavenger. The radical scavenger is present in the second component to retard or arrest the ability of the reactive monomer to self polymerize (self-polymerization is undesirable). The reactive monomer is often sold with sufficient radical scavenger. Preferably, the radical scavenger is selected from the group consisting of hydroquinone, hydroquinone monomethylether, vitamin E, and mixtures thereof.

The amount of the radical scavenger present in the second component generally will depend upon the amount of reactive monomer present. To the extent that additional amounts of radical scavenger are needed/desired, it may be added such that the second component includes about 5 parts per million (ppm) to about 500 ppm of the radical scavenger. Preferably, the radical scavenger is present in the second component in an amount of about 30 ppm to about 400 ppm, and even more preferably about 50 ppm to about 200 ppm.

In some embodiments, the bone void filler comprises beads that are disposed within the sponge matrix. The beads are settable cement beads. In one embodiment, the cement beads comprise calcium phosphate, calcium sulfate, PMMA, calcium hemihydrate, cobalt, ultra high molecular weight PEG or a combination thereof.

In some embodiments, the settable cement has a set time from about 20 seconds to about 30 minutes. In some embodiments, the set time of the settable cement is from about 20 seconds to about 20 minutes, from about 20 seconds to about 10 minutes, from about 20 seconds to about 5 minutes, from about 20 seconds to about 1 minute, from about 30 seconds to about 10 minutes, from about 30 seconds to about 5 minutes, from about 30 seconds to about 1 minute. In some embodiments, the set time of the settable cement is about 20, 22, 2.4, 26, 28, 30, 32, 34, 36, 38, 40, 42, 44, 46, 48, 50, 52, 54, 56, 58 seconds, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 minutes.

In various embodiments, the cement beads comprise synthetic ceramics comprising calcium phosphate ceramics, silicon ceramics or a combination thereof. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may also be used. In some embodiments, the ceramic is tri-calcium phosphate or biphasic calcium phosphate and silicon ceramics. In some embodiments, the ceramic is tricalcium phosphate. In some embodiments, the ceramics are a combination of a calcium phosphate ceramic and a silicon ceramic. In some embodiments, the calcium phosphate ceramic is resorbable biphasic calcium phosphate (BCP) or resorbable tri-calcium phosphate (TCP), or resorbable TCP.

In various embodiments, biphasic calcium phosphate can have a tricalcium phosphate:hydroxyapatite weight ratio of about 50:50 to about 95:5, about 70:30 to about 95:5, about 80:20 to about 90:10, or about 85:15. In some embodiments, the ceramics of the disclosure may also be oxide ceramics such as alumina ($Al_2O_3$) or zirconia ($ZrO_2$) or composite combinations of oxides and non-oxides such as silicon nitride. In some embodiments, the ceramics of the disclosure may be porous. Examples of porous ceramics are hydroxyapatite and TCP. In various embodiments, the ceramics of the disclosure are nontoxic and bioerodible such that they exhibit chemical dissolution and resorption when placed in a mammalian body. In some embodiments, the calcium phosphate is in the form of a ceramic but, may also be in the form of a calcium phosphate containing glass. In some embodiments, calcium phosphate ceramics with improved osteogenic capacity may be used alone or combined with effective amounts of other ceramics such as silicon ceramics. In some embodiments, the ceramics may include allograft cortical or cancellous bone chips. In a further aspect, the ceramics exhibit measurable dissolutions rates with porous ceramics biograding much more rapidly (degrade at a higher rate) than nonporous ceramics.

In various embodiments, the beads have a size of about 1 micron to about 200 microns. In various embodiments, the beads have a size of about 1 micron to about 300 microns, about 1 micron to about 500 microns. In some embodiments, the beads are about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 and/or 500 microns.

In various embodiments, the beads are evenly distributed throughout the sponge matrix. In some embodiments, the beads are distributed in the center of the sponge matrix. In various embodiments, the beads are distributed at the top of the sponge matrix. In some embodiments, the beads are distributed at the bottom of the sponge matrix. In various embodiments, the beads are distributed in clusters and positioned sporadically throughout the sponge matrix. In some embodiments, the beads are distributed on the outer edges of the sponge matrix.

In some embodiments, the beads comprise about 1 to 99%, about 1 to 80%, about 1 to 50%, about 1 to 30%, about 1 to 15%, about 15 to about 30%, or about 30 to about 45% by weight of the sponge matrix. In some embodiments, the beads comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% by weight of the sponge matrix.

The beads are drug loaded with a therapeutic agent comprising an antibiotic. The beads may contain one or more antibiotics. Examples of antibiotics that may be used, include but are not limited, to nitroimidazole antibiotics, tetracyclines, penicillins, cephalosporins, carbopenems, aminoglycosides (e.g., tobramycin, gentamicin, amikacin, etc.) macrolide antibiotics, lincosamide antibiotics, 4-quinolones, rifamycins, rifampin, and nitrofurantoin. Suitable specific compounds include, without limitation, ampicillin, amoxicillin, phenoxymethylpenicillin, bacampicillin, pivampicillin, carbenicillin, cloxacillin, cyclacillin, dicloxacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofioxacin, difloxacin, enoxacin, fleroxacin, norfloxacin, ofloxacin, temafloxacin, teromyocin, doxycycline, minocycline, teicoplanin, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, suifametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof.

In some embodiments, the settable cement beads are loaded with from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 to about 35 wt % of a therapeutic agent (e.g., an antibiotic) which is slowly released from the settable cement beads. The settable cement beads can be coated with the antibiotic and/or impregnated with the antibiotic. The thickness of the coating can be from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 microns.

In the present application, the antimicrobial exerts antimicrobial, which includes activity for suppressing proliferation of a microorganism, eliminating microorganisms, reducing the number thereof or decolonize, or killing the microorganisms in or at the matrix and/or target tissue site. Microorganisms include viruses, bacteria, fungi, spores, yeast or the like. Examples of microorganisms include gram-negative bacteria such as *Escherichia, Salmonella, Listeria, Bacillus, Cronobacter, Klebsiella, Proteus mirabilis, Pseudomonas* bacteria, gram-positive bacteria such as *Staphylococcus epidermidis, Staphylococcus aureus*, methicillin-resistant *Staphylococcus epidermidis*, methicillin-resistant *Staphylococcus aureus, Streptococcus pyogenes*, fungi such as *Candida albican*, or anaerobes, a combination thereof.

An effective amount of antimicrobial in the matrix is that amount for suppressing proliferation of a microorganism (bacteriostatic), eliminating microorganisms, reducing the number thereof or decolonizing, or killing the microorganisms (bactericidal) in or at the matrix and/or target tissue site. The effective amount can, in some embodiments, be measured in vitro by measuring the microorganism's MIC (minimum inhibitory concentration) when challenged with the antimicrobial. The MIC will vary depending on the organism being challenged with the antimicrobial. In some embodiments, the MIC can be from about 0.062, 0.03, 0.016, 0.008, 0.004, 0.002, 0.001, to about 0.0005 in a broth dilution with the antimicrobial.

Porosity

Bone cements typically have poor porosity, by placing the cement beads and ceramic particles in a biodegradable matrix, the porosity is enhanced and the therapeutic agent (e.g., antimicrobial) can be released from the beads, matrix and/or ceramic particles. Further, the bone cavity can be filled.

In some embodiments, the ceramic particles can be coated, impregnated, or loaded with the therapeutic agent and then these particles loaded into the matrix. In some embodiments, a biodegradable polymer (e.g., collagen) in particle form can be crosslinked after being mixed with the therapeutic agent (e.g., antimicrobial) and these particles containing the therapeutic agent and slower resorbing ceramic particles can be incorporated into a polymer matrix (e.g., collagen matrix). Therefore, as the biodegradable polymer particles in the matrix degrades therapeutic agent (e.g., antimicrobial) is released.

In some embodiments, the ceramic particles can be coated, impregnated, or loaded with the therapeutic agent (e.g., antibiotic) and then these particles can be coated with a crosslinked polymer (e.g., collagen) particles to enhance porosity of the ceramic particles. These ceramic particles that have been loaded with therapeutic agent and coated with the crosslinked polymer particles can be loaded into the matrix. Therefore, as the biodegradable polymer particles in the matrix degrades therapeutic agent (e.g., antimicrobial) is released.

Additional therapeutic agents can be added to the matrix, ceramic, polymer particles, or a combination thereof. These additional agents include, but are not limited to antimicrobials, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, thyromimetic and adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, osteoinductive factors, antiarthritics, and diagnostic agents.

In some embodiments, the beads are loaded with about 1 to about 99% by weight of the therapeutic agent. In some embodiments, the beads are loaded with about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% by weight of the therapeutic agent.

In various embodiments, the beads can be designed to cause an initial burst dose of therapeutic agent within the first 24 to 72 hours after the sponge matrix has been implanted. "Initial burst" or "burst effect" "burst release" or "bolus dose" refers to the release of therapeutic agent from the beads/sponge matrix during the first 24 hours to 72 hours after the sponge matrix comes in contact with an aqueous fluid (e.g., interstitial fluid, synovial fluid, cerebral spinal fluid, etc.). The "burst effect" is believed to be due to the increased release of therapeutic agent from the beads/sponge matrix. In some embodiments, the beads have one or more burst release surfaces that releases about 10%, 15%, 20%, 25%, 30%, 35%, 45%, to about 50% of the drug over 24 or 48 hours.

The beads release the therapeutic agent via sustained release. In some embodiments, the beads release the therapeutic agent by sustained and immediate release. In some embodiments, the beads release the therapeutic agent via immediate release.

The beads degrade at a particular rate in order to release the therapeutic agent. In various embodiments, all of the beads will degrade and release the therapeutic agent in about 1 day to about 12 months (1 year), 1 day to about 11 months, 1 day to about 10 months, 1 day to about 9 months, 1 day to about 8 months, 1 day to about 7 months, 1 day to about 6 months, 1 day to about 5 months, 1 day to about 4 months, 1 day to about 3 months, 1 day to about 2 months, 1 day to about 1 month. In some embodiments, all of the beads will degrade in about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days (1 month), 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days (2 months), 61, 62, 63, 64, 65, 66, 67, 68, 69, 70, 71, 73, 74, 75, 76, 77, 78, 79, 80, 81, 82, 83, 84, 85, 86, 87, 88, 89, 90 days (3 months), 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 days (4 months), 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 days (5 months), 151, 152, 153, 154, 155, 156, 157, 158, 159, 160, 161, 162, 163, 164, 165, 166, 167, 168, 169, 170, 171, 172, 173, 174, 175, 176, 177, 178, 179, and/or 180 days (6 months).

In various embodiments, a certain percentage of the beads will degrade and release the therapeutic agent at the same time or at different times. In some embodiments, 1 to 15%, 1 to 30%, 1 to 45%, 1 to 60%, 1 to 75%, 1 to 90%, 1 to 99%, 15 to 30%, 15 to 45%, 15 to 60%, 15 to 75%, 15 to 99%, 30 to 45%, 30 to 55%, 30 to 75%, 30 to 85%, 30 to 99%, 45 to 60%, 45 to 75% 45 to 85%, 45 to 99%, 60 to 75%, 60 to 99%, 75 to 85%, 75 to 99%, or 85 to 99% of the beads will degrade and release the therapeutic agent from about 1 day to about 6 months.

In various embodiments, 1 to 15%, 1 to 30%, 1 to 45%, 1 to 60%, 1 to 75%, 1 to 90%, 1 to 99%, 15 to 30%, 15 to 45%, 15 to 60%, 15 to 75%, 15 to 99%, 30 to 45%, 30 to 55%, 30 to 75%, 30 to 85%, 30 to 99%, 45 to 60%, 45 to 75% 45 to 85%, 45 to 99%, 60 to 75%, 60 to 99%, 75 to 85%, 75 to 99%, or 85 to 99% of the beads will degrade and release the therapeutic agent from about 1 day to about 5 months, from about 1 day to about 4 months, from about 1 day to about 3 months, from about 1 day to about 2 months, from about 1 day to about 1 month, from about 3 days to about 6 months, from about 3 days to about 5 months, from about 3 days to about 4 months, from about 3 days to about 3 months, from about 3 days to about 2 months, from about 3 days to about 1 month, from about 7 days to about 6 months, from about 7 days to about 5 months, from about 7 days to about 4 months, from about 7 days to about 3 months, from about 7 days to about 2 months, from about 7 days to about it month, from about 10 days to about 6 months, from about 10 days to about 5 months, from about 10 days to about 4 months, from about 10 days to about 3 months, from about 10 days to about 2 months, from about 10 days to about 1 month, from about 14 days to about 6 months, from about 14 days to about five months, from about 14 days to about 4 months, from about 14 days to about 3 months, from about 14 days to about 2 months, from about 14 days to about 1 month, from about 21 days to about 6 months, from about 21 days to about 5 months, from about 21 days to about 4 months, from about 21 days to about 3 months, from about 21 days to about 2 months, from about 21 days to about 1 month, from about 28 days to about 6 months, from about 28 days to about 5 months, from about 28 days to about 4 months, from about 28 days to about 3 months, from about 28 days to about 2 months, from about 28 days to about 1 month, from about 35 days to about 6 months, from about 35 days to about 5 months, from about 35 days to about 4 months, from about 35 days to about 3 months, from about 35 days to about 2 months, from about 35 days to about 1 month, from about 42 days to about 6 months, from about 42 days to about 5 months, from about 42 days to about 4 months, from about 42 days to about 3 months, from about 42 days to about 2 months, from about 42 days to about 1 month, from about 49 days to about 6 months, from about 49 days to about 5 months, from about 49 days to about 4 months, from about 49 days to about 3 months, from about 49 days to about 2 months, from about 49 days to about 1 month, from about 56 days to about 6 months, from about 56 days to about 5 months, from about 56 days to about 4 months, from about 56 days to about 3 months, from about 56 days to about 2 months, from about 56 days to about 1 month, from about 61 days to about 6 months, from about 61 days to about 5 months, from about 61 days to about 4 months, from about 61 days to about 3 months, from about 61 days to about 2 months, or from about 61 days to about 1 month.

In some embodiments, 1 to 15%, 1 to 30%, 1 to 45%, 1 to 60%, 1 to 75%, 1 to 90%, 1 to 99%, 15 to 30%, 15 to 45%, 15 to 60%, 15 to 75%, 15 to 99%, 30 to 45%, 30 to 55%, 30 to 75%, 30 to 85%, 30 to 99%, 45 to 60%, 45 to 75% 45 to 85%, 45 to 99%, 60 to 75%, 60 to 99%, 75 to 85%, 75 to 99%, or 85 to 99% of the beads will degrade and release the therapeutic agent in about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days (1 month), 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days (2 months), 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days (3 months), 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 days (4 months), 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 days (5 months), 151, 152, 153, 154, 155, 156, 157, 158, 159, 160, 161, 162, 163, 164, 165, 166, 167, 168, 169, 170, 171, 172, 173, 174, 175, 176, 177, 178, 179, and/or 180 days (6 months).

Particles

In some embodiments, the bone void filler comprises particles that are disposed within the sponge matrix. In various embodiments, the particles are disposed within the sponge matrix, along with the cement beads loaded with the therapeutic agent, as described above. In some embodiments, biodegradable collagen particles admixed with the therapeutic agent and cross-linked are disposed in the collagen sponge matrix with ceramic particles. In some embodiments, ceramic particles are either adsorbed with the therapeutic agent and coated with collagen that is cross-linked, or coated with a settable cement loaded with the therapeutic agent. The ceramic particles are then disposed within the collagen sponge matrix.

In various embodiments, the particles are slow resorbing ceramic particles. In some embodiments, the particles are biodegradable. In some embodiments, the particles are collagen particles. In some embodiments, insoluble collagen can be used and can be derived from natural tissue sources, (e.g. xenogeneic, allogenic, or autogenic relative to the recipient human or other patient) or recombinantly prepared. In some embodiments, the collagen can be atelopeptide collagen and/or telopeptide collagen. Still further, either or both of non-fibrillar and fibrillar collagen can be used. In some embodiments, naturally-derived or recombinant human collagen materials are also suitable for the particles.

In some embodiments, the particles are chemically cross-linked collagen. Crosslinked solid collagen particles can be used in combination with non-crosslinked collagen particles, where the non-crosslinked collagen can be solid (insoluble) or soluble collagen, or combinations thereof. Suitable cross-linking agents include, but are not limited to, mono- and dialdehydes, including glutaraldehyde and formaldehyde; polyepoxy compounds such as glycerol; sugars such as glucose. In one embodiment, the crosslinking agent is glycerol.

In some embodiments, the collagen can be from various collagen sources including human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof. In some embodiments, the collagen is porous.

In some embodiments, biodegradable collagen particles are admixed with a therapeutic agent, such as an antibiotic. In some embodiments, ceramic particles are adsorbed with a therapeutic agent, such as an antibiotic and coated with collagen that is cross-linked. In some embodiments, ceramic particles are coated with a settable cement loaded with a therapeutic agent, such as an antibiotic. In some embodiments, particles are drug loaded with a therapeutic agent comprising an antibiotic. Particles may contain one or more antibiotics. Examples of antibiotics that may be used, include but are not limited, to nitroimidazole antibiotics, tetracyclines, penicillins, cephalosporins, carbopenems, aminoglycosides, macrolide antibiotics, lincosamide antibiotics, 4-quinolones, rifamycins and nitrofurantoin. Suitable specific compounds include, without limitation, ampicillin, amoxicillin, benzylpenicillin, phenoxymethylpenicillin, bacampicillin, pivampicillin, carbenicillin, cloxacillin, cyclacillin, methicillin, oxacillin, piperacillin, ticarcillin, flucloxacillin, cefuroxime, cefetamet, cefetrame, cefixine, cefoxitin, ceftazidime, ceftizoxime, latamoxef, cefoperazone, ceftriaxone, cefsulodin, cefotaxime, cephalexin, cefaclor, cefadroxil, cefalothin, cefazolin, cefpodoxime, ceftibuten, aztreonam, tigemonam, erythromycin, dirithromycin, roxithromycin, azithromycin, clarithromycin, clindamycin, paldimycin, lincomycirl, vancomycin, spectinomycin, tobramycin, paromomycin, metronidazole, tinidazole, ornidazole, amifloxacin, cinoxacin, ciprofloxacin, difloxacin, enoxacin, fleroxacin, norfloxacin, ofloxacin, temafloxacin, teromyocin, doxycycline, minocycline, tetracycline, chlortetracycline, oxytetracycline, methacycline, rolitetracyclin, nitrofurantoin, nalidixic acid, gentamicin, rifampicin, amikacin, netilmicin, imipenem, cilastatin, chloramphenicol, furazolidone, nifuroxazide, sulfadiazin, sulfametoxazol, bismuth subsalicylate, colloidal bismuth subcitrate, gramicidin, mecillinam, cloxiquine, chlorhexidine, dichlorobenzylalcohol, methyl-2-pentylphenol and any combination thereof.

Additional therapeutic agents include, but are not limited to antimicrobials, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, thyromimetic and adrenergics, antihypertensive agents, cholnergics, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, non-steroidal anti-inflammatory agents, steroidal anti-inflammatory agents, antioxidants, vaso-active agents, bone-active agents, osteogenic factors, osteoinductive factors, antiarthritics, and diagnostic agents.

In some embodiments, the particles are loaded with about 1 to about 99% by weight of the therapeutic agent. In some embodiments, the particles are loaded with about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% by weight of the therapeutic agent.

In various embodiments, the particles can be designed to cause an initial burst dose of therapeutic agent within the first 24 to 72 hours after the sponge matrix has been implanted. "Initial burst" or "burst effect" "burst release" or "bolus dose" refers to the release of therapeutic agent from the particles/beads/sponge matrix during the first 24 hours to 72 hours after the sponge matrix comes in contact with an aqueous fluid (e.g., interstitial fluid, synovial fluid, cerebral spinal fluid, etc.). The "burst effect" is believed to be due to the increased release of therapeutic agent from the particles/beads/sponge matrix. In some embodiments, the particles have one or more burst release surfaces that releases about 10%, 15%, 20%, 25%, 30%, 35%, 45%, to about 50% of the drug over 24 or 48 hours.

The particles release the therapeutic agent via sustained release. In some embodiments, the particles release the therapeutic agent by sustained and immediate release. In some embodiments, the particles release the therapeutic agent via immediate release.

The particles degrade at a particular rate in order to release the therapeutic agent. In various embodiments, all of the particles will degrade and release the therapeutic agent in about 1 day to about 12 months (1 year), 1 day to about 11 months, 1 day to about 110 months, 1 day to about 9 months, 1 day to about 8 months, 1 day to about 7 months, 1 day to about 6 months, 1 day to about 5 months, 1 day to about 4 months, 1 day to about 3 months, 1 day to about 2 months, 1 day to about 1 month. In some embodiments, all of the particles will degrade in about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days (1 month), 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days (2 months), 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days (3 months), 91, 92, 93, 94, 95, 96, 97, 98, 99, 100, 101, 102, 103, 104, 105, 106, 107, 108, 109, 110, 111, 112, 113, 114, 115, 116, 117, 118, 1119, 120 days (4 months), 121, 122, 1123, 124, 125, 1126, 127, 128, 129, 130, 131, 132, 133, 134, 135, 136, 137, 138, 139, 140, 141, 142, 143, 144, 145, 146, 147, 148, 149, 150 days (5 months), 151, 152, 153, 154, 155, 156, 157, 158, 159, 160, 161, 162, 163, 164, 165, 166, 167, 168, 169, 170, 171, 172, 173, 174, 175, 176, 177, 178, 179, and/or 180 days (6 months).

In various embodiments, a certain percentage of the particles will degrade and release the therapeutic agent at the same time or at different times. In some embodiments, 1 to 15%, 1 to 30%, 1 to 45%, 1 to 60%, 1 to 75%, 1 to 90%, 1 to 99%, 15 to 30%, 15 to 45%, 15 to 60%, 15 to 75%, 15 to 99%, 30 to 45%, 30 to 55%, 30 to 75%, 30 to 85%, 30 to 99%, 45 to 60%, 45 to 75% 45 to 85%, 45 to 99%, 60 to 75%, 60 to 99%, 75 to 85%, 75 to 99%, or 85 to 99% of the particles will degrade and release the therapeutic agent from about 1 day to about 6 months.

In various embodiments, 1 to 15%, 1 to 30%, 1 to 45%, 1 to 60%, 1 to 75%, 1 to 90%, 1 to 99%, 15 to 30%, 15 to 45%, 15 to 60%, 15 to 75%, 15 to 99%, 30 to 45%, 30 to 55%, 30 to 75%, 30 to 85%, 30 to 99%, 45 to 60%, 45 to 75% 45 to 85%, 45 to 99%, 60 to 75%, 60 to 99%, 75 to 85%, 75 to 99%, or 85 to 99% of the particles will degrade and release the therapeutic agent from about 1 day to about 5 months, from about 1 day to about 4 months, from about 1 day to about 3 months, from about 1 day to about 2 months, from about 1 day to about 1 month, from about 3 days to about 6 months, from about 3 days to about 5 months, from about 3 days to about 4 months, from about 3 days to about 3 months, from about 3 days to about 2 months, from about 3 days to about 1 month, from about 7 days to about 6 months, from about 7 days to about 5 months, from about 7 days to about 4 months, from about 7 days to about 3 months, from about 7 days to about 2 months, from about 7 days to about 1 month, from about 10 days to about 6 months, from about 10 days to about 5 months, from about 10 days to about 4 months, from about 10 days to about 3 months, from about 10 days to about 2 months, from about 10 days to about 1 month, from about 14 days to about 6 months, from about 14 days to about five months, from about 14 days to about 4 months, from about 14 days to about 3 months, from about 14 days to about 2 months, from about 14 days to about 1 month, from about 21 days to about 6 months, from about 21 days to about 5 months, from about 21 days to about 4 months, from about 21 days to about 3 months, from about 21 days to about 2 months, from about 21 days to about 1 month, from about 28 days to about 6 months, from about 28 days to about 5 months, from about 28 days to about 4 months, from about 28 days to about 3 months, from about 28 days to about 2 months, from about 28 days to about 1 month, from about 35 days to about 6 months, from about 35 days to about 5 months, from about 35 days to about 4 months, from about 35 days to about 3 months, from about 35 days to about 2 months, from about 35 days to about 1 month, from about 42 days to about 6 months, from about 42 days to about 5 months, from about 42 days to about 4 months, from about 42 days to about 3 months, from about 42 days to about 2 months, from about 42 days to about 1 month, from about 49 days to about 6 months, from about 49 days to about 5 months, from about 49 days to about 4 months, from about 49 days to about 3 months, from about 49 days to about 2 months, from about 49 days to about 1 month, from about 56 days to about 6 months, from about 56 days to about 5 months, from about 56 days to about 4 months, from about 56 days to about 3 months, from about 56 days to about 2 months, from about 56 days to about 1 month, from about 61 days to about 6 months, from about 61 days to about 5 months, from about 61 days to about 4 months, from about 61 days to about 3 months, from about 61 days to about 2 months, or from about 61 days to about 1 month.

In some embodiments, 1 to 15%, 1 to 30%, 1 to 45%, 1 to 60%, 1 to 75%, 1 to 90%, 1 to 99%, 15 to 30%, 15 to 45%, 15 to 60%, 15 to 75%, 15 to 99%, 30 to 45%, 30 to 55%, 30 to 75%, 30 to 85%, 30 to 99%, 45 to 60%, 45 to 75% 45 to 85%, 45 to 99%, 60 to 75%, 60 to 99%, 75 to 85%, 75 to 99%, or 85 to 99% of the particles will degrade and release the therapeutic agent in about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 days (1 month), 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 days (2 months), 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days (3 months), 91, 92, 93, 94, 95, 96, 97, 98, 99, 100, 101, 102, 103, 104, 105, 106, 107, 108, 109, 110, 111, 112, 113, 114, 115, 116, 117, 118, 119, 120 days (4 months), 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 days (5 months), 151, 152, 153, 154, 155, 156, 157, 158, 159, 160, 161, 162, 163, 164, 165, 166, 167, 168, 169, 170, 171, 172, 173, 174, 175, 176, 177, 178, 179, and/or 180 days (6 months).

In various embodiments, the particles are ceramic particles that comprise hydroxyapatite and/or tricalcium phosphate. In some embodiments, the ceramic particles comprises a ratio of hydroxyapatite and/or tricalcium phosphate at about 10:1, 9:1, 8:1, 7:1, 6:1, 5:1, 4:1, 3:1, 2:1, 1:10, 1:9, 1:8, 1:7, 1:6, 1:5, 1:4, 1:3, 1:2, or 1:1.

In various embodiments, the ceramic can contain other calcium phosphate ceramic materials, such as dicalcium phosphate, amorphous hydroxyapatite, crystalline hydroxyapatite, coralline hydroxyapatite, hydroxyapatite e.g., ETEX CaP, silicate containing ceramics or a combination thereof. In some embodiments the ceramic material comprises fast resorbing $CaPO_4$. In some embodiments, it may also be possible to include some polymer (e.g., natural or synthetic degradable polymer) in the ceramic. Biological glasses such as calcium-silicate-based bioglass, silicon calcium phosphate, biphasic calcium phosphate, calcium sulfate, silicon carbide, silicon nitride ($Si_3N_4$), and biocompatible ceramics may also be used.

In some embodiments, ceramic particles are either adsorbed with the therapeutic agent and coated with collagen that is cross-linked, or coated with a settable cement loaded with the therapeutic agent. The coating thickness may be thin, for example, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50 microns to thicker coatings 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100 microns to delay release of the therapeutic agent from the particles. In some embodiments, the range of the coating on the particles range from about 1 to about 100 microns, from about 5 microns to about 150 microns, from about 5 microns to about 100 microns, from about 10 microns to about 150 microns, and from about 10 microns to about 100 microns to delay release from the particles. In various embodiments, the particles comprise multiple coatings/multi-layered coatings. In some embodiments, the particles are coated with 1, 2, 3, 4, 5, 6, 7, 8, 9 and/or 10 coatings. In some embodiments, the multiple coatings can be different thicknesses.

In some embodiments, the particles are about 1 to about 500 microns in size, about 1 to about 400, about 1 to about 300, about 1 to about 200, about 1 to about 100, about 1 to about 50 about 50 to 300, about 50 to about 200, about 50 to about 100, about 50 to about 70, about 100 to about 500, about 50 to about 400, about 50 to about 300, about 50 to about 200, about 50 to about 100, about 10 to about 50, about 10 to about 40, about 10 to about 30, about 10 to about 20, about 10 to about 15, about 5 to about 10 microns in size. In some embodiments, the particles can be the same size or different sizes from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 and/or 500 microns.

In some embodiments, the ratio of ceramic cement beads to ceramic particles disposed within the collagen sponge matrix is about 10:1, 9:1, 8:1, 7:1, 6:1, 5:1, 4:1, 3:1, 2:1, 1:1, 1:10, 1:9, 1:8, 1:7, 1:6, 1:5, 1:4, 1:3, or 1:2. In various embodiments, the ratio of collagen particles to slow resorbing ceramic particles disposed within the collagen sponge matrix is about 10:1, 9:1, 8:1, 7:1, 6:11, 5:1, 4:1, 3:1, 2:1, 1:1, 1:10, 11:9, 1:8, 1:7, 1:6, 1:5, 1:4, 1:3, or 1:2.

The particles can comprise micropores to aid in the release of the therapeutic agent. In some embodiments, some or all of the particles comprise micropores. In various embodiments, 10, 20, 30, 40, 50, 60, 70, 80, 90, 99, or 100% of the particles comprise micropores. In some embodiments, the micropores are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40 microns in size. In some embodiments, the micropores are all the same size. In some embodiments, the micropores are different sizes. In some embodiments, 10, 20, 30, 40, 50, 60, 70, 80, 90, or 100% of the micropores are 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and/or 40 microns in size.

In various embodiments, the particles are evenly distributed throughout the sponge matrix. In some embodiments, the particles are distributed in the center of the sponge matrix. In various embodiments, the particles are distributed at the top of the sponge matrix. In some embodiments, the particles are distributed at the bottom of the sponge matrix. In various embodiments, the particles are distributed in clusters and positioned sporadically throughout the sponge matrix. In some embodiments, the particles are distributed on the outer edges of the sponge matrix.

In some embodiments, the particles comprise about 1 to 99%, about 1 to 80%, about 1 to 50%, about 1 to 30%, about 1 to 15%, about 15 to about 30%, or about 30 to about 45% by weight of the sponge matrix. In some embodiments, the particles comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% by eight of the sponge matrix.

Bone Void Filler Device

Figure 2:
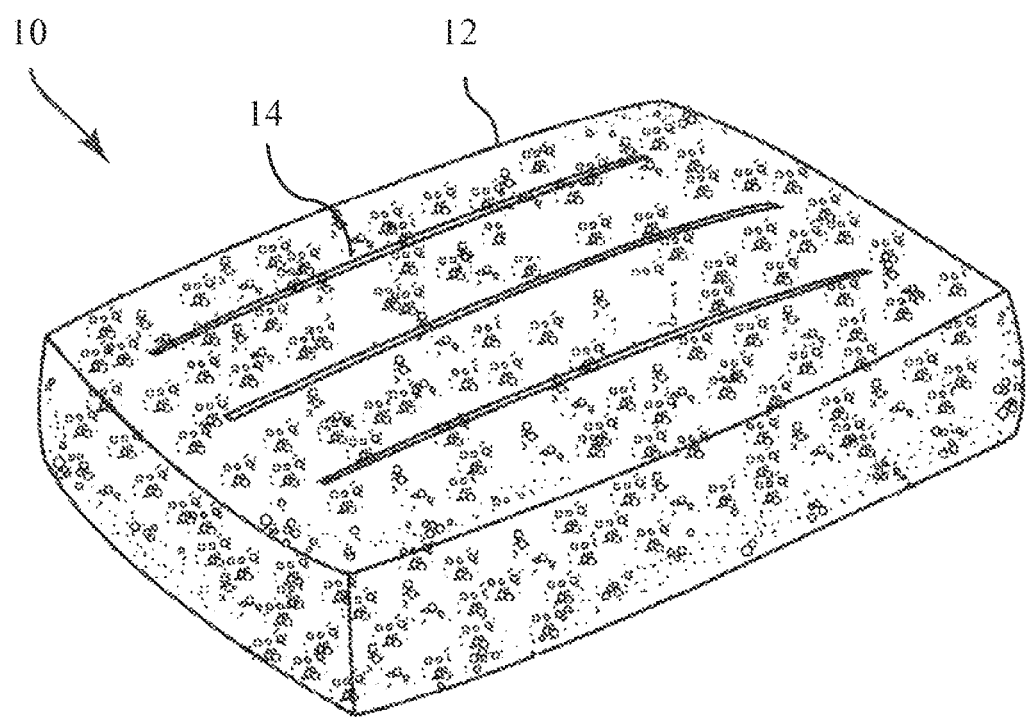
FIG. 2 depicts the bone void filler of FIG. 1, with score lines so that the bone void filler may be segmented for use, if desired.
Figure 3:
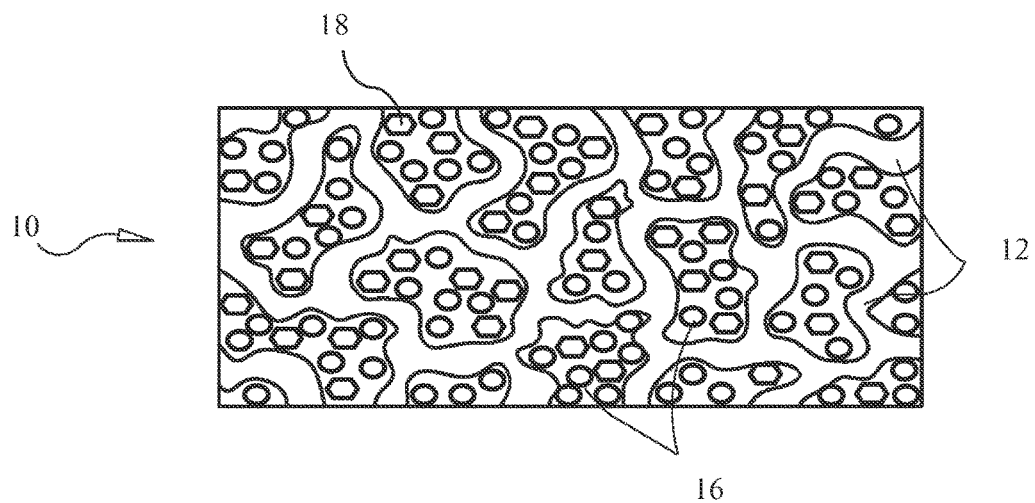
FIG. 3 depicts the bone void filler material of FIG. 1. Cement beads loaded with a therapeutic agent and ceramic particles are disposed within a collagen sponge matrix.

In some embodiments, a bone void filler material 10 is provided, as shown in FIGS. 1-5. The bone void filler material is configured for sustained release of a therapeutic agent, such as an antibiotic. The bone void filler material comprises a collagen sponge matrix 12, cement beads 16 loaded with the therapeutic agent, and slower resorbing ceramic particles 18. In some embodiments, the cement beads and the ceramic particles are disposed within the collagen sponge matrix, as shown in FIG. 3. In some embodiments, the cement beads are settable. In various embodiments, the cement beads are biodegradable and will release the therapeutic agent in a sustained release over a period of 1 day to 1 year. In some embodiments, the cement beads are from about 1 micron to about 200 microns in size. In some embodiments, the therapeutic agent comprises an antibiotic comprising nitroimidazole, tetracyclines, penicillins, cephalosporins, carbopenems, aminoglycosides, macrolides, or lincosamides. In various embodiments, the ceramic particles comprise hydroxyapatite, tricalcium phosphate or a combination thereof. In some embodiments, the ceramic particles are slow resorbing relative to the cement beads. In some embodiments, micropores are disposed within the ceramic particles and the bone void filler material further comprises silicated ceramic, collagen and demineralized bone matrix (DBM). In some embodiments, the collagen sponge matrix alternatively comprises chitosan, keratin, alginate, hyaluronic acid or a combination thereof. In various embodiments, the collagen sponge matrix comprises pores having a size range from about 1 micron to about 1,000 microns.

Figure 4:
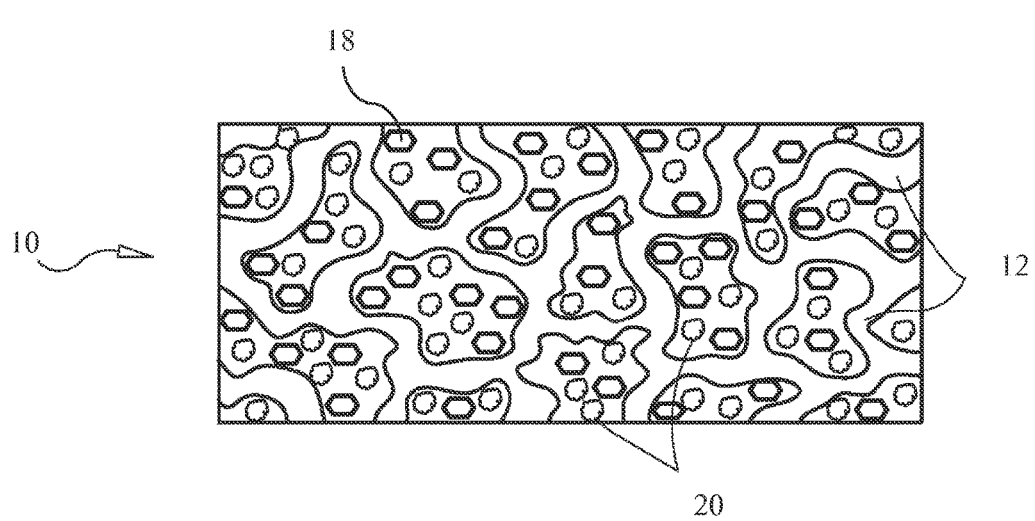
FIG. 4 depicts the bone void filler material of FIG. 1. Biodegradable collagen particles admixed with therapeutic agent and cross-linked, and ceramic particles are disposed within a collagen sponge matrix.

In some embodiments, a bone void filler material is provided that is configured for sustained release of a therapeutic agent, as shown in FIG. 4. The bone void filler material comprises the collagen sponge matrix, biodegradable collagen particles 20 admixed with the therapeutic agent and cross-linked, and the ceramic particles. The collagen particles and the ceramic particles are disposed within the collagen sponge matrix. In some embodiments, the ceramic particles are slow resorbing relative to the biodegradable collagen particles, and the biodegradable collagen particles degrade over time to release the therapeutic agent in a sustained release. In some embodiments, the collagen particles are cross-linked with a cross-linking agent comprising glutaraldehyde, formaldehyde, glycerol or glucose. In various embodiments, the ceramic particles comprise hydroxyapatite, tricalcium phosphate or a combination thereof. In some embodiments, the ceramic particles are from about 1 micron to about 800 microns in size.

Figure 5:
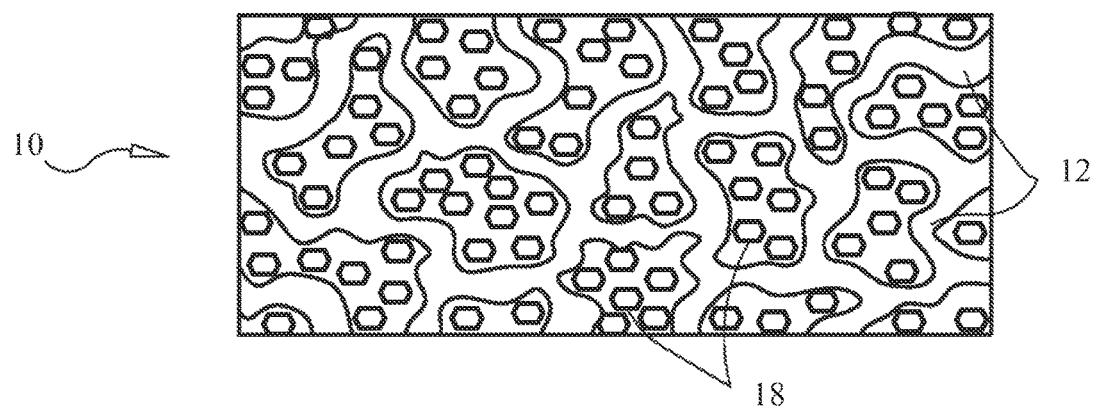
FIG. 5 depicts the bone void filler material of FIG. 1. Ceramic particles are either (i) adsorbed with therapeutic agent and coated with cross-linked collagen, or (ii) coated with a settable cement loaded with therapeutic agent. The ceramic particles are disposed within a collagen sponge matrix.

In some embodiments, a bone void filler material is provided that is configured for sustained release of a therapeutic agent, as shown in FIG. 5. The bone void filler material comprises the collagen sponge matrix; and ceramic particles that are either adsorbed with the therapeutic agent and coated with collagen that is cross-linked, or coated with a settable cement loaded with the therapeutic agent. The ceramic particles are disposed within the collagen sponge matrix. In some embodiments, the therapeutic agent is released from the ceramic particles in a sustained release over a period of 1 day to 3 months. In some embodiments, the collagen is cross-linked via a cross-linking agent comprising glutaraldehyde, formaldehyde, glycerol or glucose. In various embodiments, the ceramic particles are slow resorbing and comprise hydroxyapatite, tricalcium phosphate or a combination thereof. In some embodiments, the settable cement coating is from 1 micron to 100 microns thick. In various embodiments, micropores are disposed within the ceramic particles.

In some embodiments, the sponge matrix comprises score lines or perforations 14 so that the bone void filler may be segmented into sections for use, if desired, as shown in FIG. 2. A surgeon may select the number of sections desired for placement and cut and/or pull/tear along the score lines or perforations providing the desired number of sections. In various embodiments, the sponge matrix can comprise 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, or 60 scores lines.

Bone Material

In some embodiments, demineralized bone matrix (DBM) may be added to the bone void filler. For example, DBM may be added to the sponge matrix, the beads and/or the particles. In some embodiments, the bone material that the DBM derives from is lyophilized. In various embodiments, the DBM is a demineralized bone fiber and is cartridge milled, having a ribbon-like shape and increased surface area. In some embodiments, the DBM bone fibers have a diameter from about 50 microns to about 350 microns. In some embodiments, the fibers have an aspect ratio of from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In some embodiments, the fibers can comprise blood, water, saline or a combination thereof.

In some embodiments, bone material comprising a coherent mass of cartridge milled and demineralized bone fibers can be added to the bone void filler. In some embodiments, the bone material comprises cortical bone, cancellous bone, cortico-cancellous bone, or mixtures thereof. In some embodiments, the bone material is obtained from autogenous bone, allogenic bone, xenogeneic bone, or mixtures thereof. In some embodiments, the bone material is a cube, square, fiber, chip, rectangular, circular, disc and/or cylinder shape. In some embodiments, the bone material can be a cohesive mass of bone fibers that are entangled and surface to surface interact between adjacent bone fibers.

The bone material aids the bone void filler with resorbing/remodeling and being replaced by host bone during the healing process. In some embodiments, the bone material disclosed herein includes additional additives, such as synthetic ceramics and/or bioerodible polymers, which produce high concentrations of calcium, phosphate and silicon ions that act as a nidus for de-novo bone formation.

The bone material may be a combination of fibers of bone matrix from allograft bone and fibers of non-allograft bone material. The fibers of the non-allograft bone material comprise non-fibrous demineralized bone matrix particles embedded within or dispersed on the fibers of the non-allograft bone material. The ratio of fibers of demineralized bone matrix from allograft material to fibers of non-allograft material ranges from about 20:80 to about 70:30. In one embodiment, the ratio of fibers from allograft material to fibers of non-allograft material ranges from about 40:60 to about 60:40. In one embodiment, the ratio of fibers of demineralized bone matrix from allograft material to fibers of non-allograft material is about 50:50.

In some embodiments, the demineralized bone material includes particles that are non-fibrous. In some embodiments, the particles are powders, microspheres, sponges, pastes, gels, and/or granules. In one embodiment, the particles are powders.

In some embodiments, the demineralized bone material particles comprise from about 1 to about 70 micrometers or from about 125 to about 250 micrometers. In some embodiments, the demineralized bone material particles comprise about 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248 and/or 250 microns.

In various embodiments, the fibers have an aspect ratio of length to width from about 50:1 to about 1000:1, from about 50:1 to about 950:1, from about 50:1 to about 750:1, from about 50:1 to about 500:1, from about 50:1 to about 250:1, from about 50:1 to about 100:1, from about 10:1 to about 50:1, or from about 5:1 to about 10:1. In other embodiments, the fibers have an aspect ratio of length to width of about 4:1, 17:1, or 23:1.

DBM particles for use in the present disclosure can be obtained commercially or can be prepared by known techniques. In general, advantageous, osteoinductive DBM materials can be prepared by decalcification of cortical and/or cancellous bone, often by acid extraction. This process can be conducted so as to leave collagen, noncollagenous proteins, and growth factors together in a solid matrix. Methods for preparing such bioactive demineralized bone matrix are known, in respect of which reference can be made to U.S. Pat. Nos. 5,073,373; 5,484,601; and 5,284,655, as examples. DBM products are also available commercially, including for instance, from sources such as Regeneration Technologies, Inc. (Alachua, Fla.), The American Red Cross (Arlington, Va.), and others. For the purposes of this disclosure, any shape and particle size of DBM may be used. This includes DBM in the form of fragments, slices, pellets, shavings, granules, fibers, or powder a well as demineralized whole bones. In various embodiments, the demineralized bone is of a small particle size, and in the form of powder. In certain embodiments, the bone particles can have an average particle size of less than about 100 to about 1000 microns. For instance, the bone particles can have particle sizes in the range of 50 to 850 microns. Bone particles and fibers that are solely osteoconductive can be prepared using similar techniques that have been modified or supplemented to remove or inactivate (e.g. by crosslinking or otherwise denaturing) components in the bone matrix responsible for osteoinductivity. Osteoinductive and/or osteoconductive DBM materials used in the present disclosure can be derived from human donor tissue, especially in regard to implant devices intended for use in human subjects.

In regard to the incorporated materials considered on a dry weight basis, the particulate bone material can constitute about 10% to about 50% of the bone void filler, about 20% to about 40%, and about 25% to about 35% by weight. In various embodiments, particulate DBM material can constitute about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or about 50% of the bone void filler.

Additives

In some embodiments, the bone material may be combined with non-bone material additives after demineralization and/or lyophilization and before implantation into the bone void filler. For example, the bone material may be combined with a bioerodible polymer. The bioerodible polymer exhibits dissolution when placed in a mammalian body and may be hydrophilic (e.g., collagen, hyaluronic acid, polyethylene glycol). Synthetic polymers are suitable according to the present disclosure, as they are biocompatible and available in a range of copolymer ratios to control their degradation. The bone void filler may be configured to be moldable, extrudable, or substantially solid.

Any suitable shape, size, and porosity of bone void filler may be used. In various embodiments, the bone void filler comprises an osteoinductive material such as a mineralized particulated material, osteoinductive growth factors, or partially demineralized bone. The mineralized particulated material may be TCP, hydroxyapatite, mineral recovered from bones, surface demineralized bone fiber, or other material.

In some embodiments, the bone void filler may also contain other beneficial substances including for example preservatives, cosolvents, viscosity enhancing agents, ionic strength and osmolality adjusters and/or other excipients. Suitable buffering agents can also be used an include but are not limited to alkaline earth metal carbonates, phosphates, bicarbonates, citrates, borates, acetates, succinates, or others. Illustrative-specific buffering agents include for instance sodium phosphate, sodium citrate, sodium borate, sodium acetate, sodium bicarbonate, sodium carbonate, and sodium tromethanine (TRIS). These agents can be included in amounts that are effective to maintain the pH of the system at a biologically acceptable level, for instance maintaining a pH between about 6 and about 8 and preferably near neutral.

The bone void filler of the disclosure may be used alone as scaffolds of bone tissue engineering for repair, augmentation or replacement of bone tissue or as carriers for biologically active ingredients.

One of more biologically active ingredients may be added to the bone void filler. These active ingredients may or may not be related to the bone repair capabilities of the bone void filler. Suitable active ingredients hemostatic agents, bone morphogenic proteins (BMPs), genes, growth differentiation factors (GDFs), or other non-collagenic proteins such as TGF-β, PDGF, ostropontin, osteonectin, cytokines, and the like.

In one embodiment, the bone void filler may include at least one BMPs, which are a class of proteins thought to have osteoinductive or growth-promoting activities on endogenous bone tissue, or function as pro-collagen precursors. Known members of the BMP family include, but are not limited to, BMP-1, BMP-3, BMP-4, BMP-5, BMP-6, BMP-8, BMP-9, BMP-10, BMP-11, BMP-12, BMP-13, BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

In another embodiment, the bone void filler may include one or more Growth Differentiation Factors ("GDFs") disposed in the compartment or disposed on or in the coherent mass. Known GDFs include, but are not limited to, GDF-1, GDF-2, GDF-3, GDF-7, GDF-10, GDF-11, and GDF-15. For example, GDFs useful as isolated osteoinductive agents include, but are not limited to, the Mowing GDFs: GDF-1 polynucleotides or polypeptides corresponding to GenBank Accession Numbers M62302, AAA58501, and AAB94786, as well as mature GDF-1 polypeptides or polynucleotides encoding the same. GDF-2 polynucleotides or polypeptides corresponding to GenBank Accession Numbers BC069643, BC074921, Q9UK05, AAH69643, or AAH74921, as well as mature GDF-2 polypeptides or polynucleotides encoding the same. GDF-3 polynucleotides or polypeptides corresponding to GenBank Accession Numbers AF263538, BCO30959A, AF91389, AAQ89234, or Q9NR23, as well as mature GDF-3 polypeptides or polynucleotides encoding the same. GDF-7 polynucleotides or polypeptides corresponding to GenBank Accession Numbers AB158468, AF522369, AAP97720, or Q7Z4P5, as well as mature GDF-7 polypeptides or polynucleotides encoding the same. GDF-10 polynucleotides or polypeptides corresponding to GenBank Accession Numbers BC028237 or AAH28237, as well as mature GDF-10 polypeptides or polynucleotides encoding the same.

GDF-11 polynucleotides or polypeptides corresponding to GenBank Accession Numbers AF100907, NP005802 or 095390, as well as mature GDF-11 polypeptides or polynucleotides encoding the same. GDF-15 polynucleotides or polypeptides corresponding to GenBank Accession Numbers BC008962, BC000529, AAH00529, or NP004855, as well as mature GDF-15 polypeptides or polynucleotides encoding the same.

In some embodiments, the bone void filler contains other therapeutic agents/bioactive agents. In certain embodiments, the therapeutic agent/bioactive agent is a drug that may include, for example, antimicrobials, antibiotics, antimyobacterial, antifungals, antivirals, antineoplastic agents, antitumor agents, agents affecting the immune response, blood calcium regulators, agents useful in glucose regulation, anticoagulants, antithrombotics, antihyperlipidemic agents, cardiac drugs, thyromimetic and antithyroid drugs, adrenergics, antihypertensive agents, cholinergic, anticholinergics, antispasmodics, antiulcer agents, skeletal and smooth muscle relaxants, prostaglandins, general inhibitors of the allergic response, antihistamines, local anesthetics, analgesics, narcotic antagonists, antitussives, sedative-hypnotic agents, anticonvulsants, antipsychotics, anti-anxiety agents, antidepressant agents, anorexigenics, nonsteroidal anti-inflammatory agents, steroidal anti-inflammatory agents, antioxidants, vaso-active agents, bone-active agents, osteogenic factors, antiarthritics, and diagnostic agents.

A more complete listing of therapeutic agents/bioactive agents and specific drugs suitable for use in the present disclosure may be found in "The Merck Index: An Encyclopedia of Chemicals, Drugs, and Biologicals," Edited by Susan Budavari, et al.; and the United States Pharmacopoeia/National Formulary XXXVII/XXXII, published by the United States Pharmacopeial Convention, Inc., Rockville, Md., 2013, each of which is incorporated herein by reference.

It will be appreciated that the amount of additive used will vary depending upon the type of additive, the specific activity of the particular additive preparation employed, and the intended use of the bone void filler. The desired amount is readily determinable by the user.

Any of a variety of medically and/or surgically useful substances can be incorporated in, or associated with, the allograft bone material or non-allograft bone material either before, during, or after preparation of the bone void filler. Thus, for example when the non-allograft bone material is used, one or more of such substances may be introduced into the non-allograft bone fibers, for example, by soaking or immersing these bone fibers in a solution or dispersion of the desired substance(s).

All the composite materials according to the present disclosure can be loaded with bone marrow cells taken from the patient directly in the operating theatre while undergoing the type of orthopedic surgery that requires their application, or a few days before the graft is due to be performed, to allow the purification and expansion in vitro of the mesenchymal cells in the marrow, so that these can then be loaded into the structure that is the subject of the present disclosure, either undifferentiated and/or partially or completely differentiated into osteoblasts/osteocytes.

Alternatively, the bone void filler can also be loaded with allogenic bone marrow cells, possibly purified, expanded and differentiated in vitro. In a further aspect, the bone void filler further comprises stem cells, osteogenic cells and/or osteoprogenic cells.

Methods of Treatment

In some embodiments, a method is provided for treating bone at a surgical site. The method includes administering a bone void filler material for sustained release of a therapeutic agent to a surgical site, the bone void filler material comprising a biodegradable matrix having ceramic particles and cement beads disposed within the matrix, the cement beads loaded with the therapeutic agent to cause sustained release of the therapeutic agent.

In some embodiments, the biodegradable matrix comprises collagen, chitosan, keratin, alginate, hyaluronic acid or a combination thereof. In some embodiments, the biodegradable matrix comprises collagen, and the collagen comprises human collagen type I, human collagen type II, human collagen type III, human collagen type IV, human collagen type V, human collagen type VI, human collagen type VII, or a combination thereof. In some embodiments, the cement beads are settable and comprise a prepolymerized styrene acrylates, polymethacrylate, polyethacrylate, polybutylmethacrylate, and copolymers thereof. In some embodiments, the therapeutic agent is released from the cement beads in a sustained release over a period of at least 3 days to 1 year. In some embodiments, the cement beads are from about 1 micron to about 200 microns in size. In some embodiments, the therapeutic agent comprises an antibiotic comprising minocycline, tetracycline, vancomycin, gentamicin, tobramycin, amikacin, rifampin, teicoplanin or a combination thereof. In some embodiments, the ceramic particles comprise hydroxyapatite, tricalcium phosphate or a combination thereof. In some embodiments, the bone void filler material further comprises silicated ceramic, demineralized bone matrix (DBM) or a combination thereof. In some embodiments, the biodegradable matrix is porous and comprises pores having a size range from about 1 micron to about 1,000 microns.

In some embodiments, a method is provided for treating bone at a surgical site. The method includes administering a bone void filler material for sustained release of a therapeutic agent to a surgical site, the hone void filler material comprising a biodegradable matrix having collagen particles and ceramic particles disposed within the matrix, the collagen particles are admixed with the therapeutic agent and cross-linked to cause sustained release of the therapeutic agent. In some embodiments, the biodegradable matrix is a collagen sponge matrix, the ceramic particles are slow resorbing relative to the biodegradable collagen particles, and/or the collagen particles degrade over time to release the therapeutic agent. In some embodiments, the collagen particles are cross-linked with a cross-linking agent comprising glutaraldehyde, formaldehyde, glycerol or glucose. In some embodiments, the ceramic particles comprise hydroxyapatite, tricalcium phosphate or a combination thereof, and/or the ceramic particles are from about 1 micron to about 800 microns in size. In some embodiments, the bone void filler material is porous and comprises pores having a size range from about 1 micron to about 800 microns.

In some embodiments, a method is provided for treating bone at a surgical site. The method includes administering a bone void filler material for sustained release of a therapeutic agent to a surgical site, the bone void filler material comprising a biodegradable matrix having ceramic particles, the ceramic particles are loaded with the therapeutic agent and coated with cross-linked collagen to cause sustained release of the therapeutic agent.

In some embodiments, the biodegradable matrix comprises collagen, and/or the therapeutic agent is released from the ceramic particles over a period of 1 day to 3 months. In some embodiments, the ceramic particles are slow resorbing and comprise hydroxyapatite, tricalcium phosphate or a combination thereof. In some embodiments, the cross-linked collagen coating is from 1 micron to 100 microns thick. In some embodiments, the micropores are disposed within the ceramic particles.

Illustrative bone repair sites that can be treated with the bone void filler of the disclosure include, for instance, those resulting from injury, defects brought about during the course of surgery, infection, malignancy or developmental malformation. The bone void filler can be used in a wide variety of orthopedic, periodontal, neurosurgical and oral and maxillofacial surgical procedures including, but not limited to the repair of simple and compound fractures and non-unions; external and internal fixations; joint reconstructions such as arthrodesis; general arthroplasty; cup arthroplasty of the hip; femoral and humeral head replacement; femoral head surface replacement and total joint replacement; repairs of the vertebral column including spinal fusion and internal fixation; tumor surgery, e.g., deficit filing; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay osteoimplants; implant placement and revision; sinus lifts; cosmetic enhancement; etc. Specific bones which can be repaired or replaced with the bone void filler include, but are not limited to the ethmoid; frontal; nasal; occipital; parietal; temporal; mandible; maxilla; zygomatic; cervical vertebra; thoracic vertebra; lumbar vertebra; sacrum; rib; sternum; clavicle; scapula; humerus; radius; ulna; carpal bones; metacarpal bones; phalanges; ilium; ischium; pubis; femur; tibia; fibula; patella; calcaneus; tarsal and metatarsal bones.

In accordance with certain aspects of the disclosure, the bone void filler can be incorporated in, on or around a load bearing implants such as spinal implants, hip implants (e.g. in or around implant stems and/or behind acetabular cups), knee implants (e.g. in or around stems). In some embodiments, the bone void filler can be incorporated in, on or around a load-bearing spinal implant device having a compressive strength of at least about 10000 N, such as a fusion cage, dowel, or other device potentially having a pocket, chamber or other cavity tier containing an osteoinductive composition, and used in a spinal fusion such as an interbody fusion.

Methods for preparing DBM are well known in the art as described, e.g. U.S. Pat. Nos. 5,314,476, 5,507,813, 5,073, 373, and 5,405,390, each incorporated herein by reference. Methods for preparing ceramic powders of calcium phosphate and/or hydroxyapatite are described, e.g. in U.S. Pat. Nos. 4,202,055 and 4,713,076, each incorporated herein by reference.

The bone void filler of the disclosure can be used alone, as bone grafting materials, as scaffolds for bone tissue engineering for repair, augmentation and replacement of bone tissue or as carriers of growth factors, or carriers of genes.

It should be understood that the forgoing relates to exemplary embodiments of the disclosure and that modifications may be made without departing from the spirit and scope of the disclosure as set forth in the following claims.

What is claimed is:

1. A bone void filler material for sustained release of a therapeutic agent, the bone void filler material comprising a biodegradable matrix comprising collagen having ceramic particles and cement beads, the cement beads being settable and having a setting time from about 20 seconds to about 30 minutes, the cement beads comprising from about 1 to about 30% by weight of the matrix and loaded with from about 1 to about 35% by weight of a therapeutic agent to cause a burst release of the therapeutic agent, the cement beads having a size of about 1 micron to about 200 microns, the ceramic particles having a particle size of 1 micron to 200 microns and also being loaded with the therapeutic agent, the ceramic particles are coated with cross-linked collagen, the coating of the cross-linked collagen being from 1 micron to 5 microns thick to cause sustained release of the therapeutic agent, wherein the biodegradable matrix is in sponge form and the ceramic particles comprise 1% to 5% by weight of the biodegradable matrix, wherein the ceramic particles have a burst release surface that releases about 10% to about 30% of the therapeutic agent over 24 or 48 hours and the cement beads have a burst release surface that releases about 10% to about 50% of the therapeutic agent over 24 or 48 hours, wherein the bone void filler material is osteoinductive and osteoconductive and contains demineralized bone matrix (DBM) particles.

2. A bone void filler material according to claim 1, wherein the biodegradable matrix further comprises chitosan, keratin, alginate, hyaluronic acid or a combination thereof.

3. A bone void filler material according to claim 1, wherein the collagen in the biodegradable matrix comprises human collagen type I, human collagen type II, human collagen type III, human collagen type IV, human collagen type V, human collagen type VI, human collagen type VII, or a combination thereof.

4. A bone void filler material according to claim 1, wherein the cement beads comprise a prepolymerized styrene acrylates, polymethacrylate, polyethacrylate, polybutylmethacrylate, or copolymers thereof.

5. A bone void filler material according to claim 1, wherein the therapeutic agent is released over a period of at least 3 days to 1 year.

6. A bone void filler material according to claim 1, wherein the therapeutic agent comprises an antibiotic comprising minocycline, tetracycline, vancomycin, gentamicin, tobramycin, amikacin, rifampin, teicoplanin or a combination thereof.

7. A bone void filler material according to claim 1, wherein the ceramic particles comprise hydroxyapatite, tricalcium phosphate or a combination thereof.

8. A bone void filler material according to claim 1, wherein the biodegradable matrix is porous and comprises pores having a size range from about 1 micron to about 1,000 microns.

9. A bone void filler material for sustained release of a therapeutic agent, the bone void filler material comprising a biodegradable matrix having cement beads, collagen particles and ceramic particles, the cement beads being settable and having a setting time from about 20 seconds to about 30 minutes, the cement beads comprising from about 1 to about 15% by weight of the matrix and loaded with from about 1 to about 35% by weight of a therapeutic agent to cause a burst release of the therapeutic agent, the cement beads having a size of about 1 micron to about 200 microns, the collagen particles having an average maximum particle size diameter of 0.5 mm to 2 mm and also containing the therapeutic agent, the ceramic particles also containing the therapeutic agent and having a particle size of 1 micron to 200 microns and being coated with crosslinked collagen, the crosslinked collagen coating having a thickness of 1 micron to 5 microns, wherein the biodegradable matrix is in sponge form and the ceramic particles comprise 1% to 5% by weight of the biodegradable matrix, wherein the ceramic particles and cement beads are distributed in clusters and positioned sporadically throughout the matrix, wherein the ceramic particles have a burst release surface that releases about 10% to about 30% of the therapeutic agent over 24 or 48 hours and the cement beads have a burst release surface that releases about 10% to about 50% of the therapeutic agent over 24 or 48 hours.

10. A bone void filler material according to claim 9, wherein the ceramic particles are slow resorbing relative to the collagen particles.

11. A bone void filler material according to claim 9, wherein the collagen particles are cross-linked with a cross-linking agent comprising glutaraldehyde, formaldehyde, glycerol or glucose.

12. A bone void filler material according to claim 9, wherein the ceramic particles comprise hydroxyapatite, tricalcium phosphate or a combination thereof.

13. A bone void filler material according to claim 9, wherein the bone void filler material is porous and comprises pores having a size range from about 1 micron to about 800 microns.

14. A bone void filler material for sustained release of a therapeutic agent, the bone void filler material comprising a biodegradable matrix comprising cement beads, and collagen, the cement beads being settable and having a setting time from about 20 seconds to about 30 minutes, the cement beads comprising from about 1 to about 15% by weight of the matrix and loaded with from about 1 to about 35% by weight of a therapeutic agent to cause a burst release of the therapeutic agent, the cement beads having a size of about 1 micron to about 200 microns, the collagen having ceramic particles, the ceramic particles also being loaded with the therapeutic agent in an amount of about 20% to about 80% by weight based on a total weight of the ceramic particles, the ceramic particles having a particle size of 1 micron to 200 microns and coated with cross-linked collagen to cause sustained release of the therapeutic agent, the cross-linked collagen coating having a thickness of 1 micron to 5 microns, wherein the biodegradable matrix is in sponge form and the ceramic particles comprise 1% to 5% by weight of the biodegradable matrix, wherein the therapeutic agent comprises an antibiotic, wherein the ceramic particles have a burst release surface that releases about 10% to about 30% of the therapeutic agent over 24 or 48 hours and the cement beads have a burst release surface that releases about 10% to about 50% of the therapeutic agent over 24 or 48 hours.

15. A bone void filler material according to claim 14, wherein the therapeutic agent is released from the ceramic particles over a period of 1 day to 3 months.

16. A bone void filler material according to claim 14, wherein the ceramic particles are slow resorbing and comprise hydroxyapatite, tricalcium phosphate or a combination thereof.

17. A bone void filler material according to claim 14, wherein micropores are disposed within the ceramic particles.

18. A bone void filler according to claim 1, wherein the therapeutic agent is released over a period of at least 3 days to about 6 months.

* * * * *

UNITED STATES PATENT AND TRADEMARK OFFICE
CERTIFICATE OF CORRECTION

PATENT NO. : 10,029,031 B2
APPLICATION NO. : 14/924862
DATED : July 24, 2018
INVENTOR(S) : McKay It is certified that error appears in the above-identified patent and that said Letters Patent is hereby corrected as shown below:

In the Specification

Column 2, Line 30, delete "hone" and insert -- bone --, therefor.

Column 4, Line 56, delete "conical," and insert -- cortical, --, therefor.

Column 6, Line 8, delete "hone" and insert -- bone --, therefor.

Column 6, Line 15, delete "in some" and insert -- In some --, therefor.

Column 6, Line 53, delete "4%, 1%," and insert -- 4%, 3%, --, therefor.

Column 6, Line 60, delete "50:11" and insert -- 50:1 --, therefor.

Column 7, Line 2, delete "hone" and insert -- bone --, therefor.

Column 9, Line 41, delete "type HI," and insert -- type III, --, therefor.

Column 9, Line 57, delete "type HI," and insert -- type III, --, therefor.

Column 10, Line 46, delete "poly-anhydrides)." and insert -- polyanhydrides). --, therefor.

Column 10, Line 58, delete "derinatan" and insert -- dermatan --, therefor.

Column 10, Line 61, delete "polyglycolide," and insert -- polyglycolide, PLGA, --, therefor.

Column 11, Line 5, delete "(Da) In" and insert -- (Da). In --, therefor.

Column 11, Line 18, delete "7, 9," and insert -- 7, 8, 9, --, therefor.

Signed and Sealed this
Twenty-third Day of July, 2019

Andrei Iancu
*Director of the United States Patent and Trademark Office*

Column 11, Line 51, delete "microns, in" and insert -- microns. In --, therefor.

Column 12, Line 29, delete "6×1.0$^5$" and insert -- 6×10$^5$ --, therefor.

Column 13, Line 64, delete "PEG monoactylates," and insert -- PEG monoacrylates, --, therefor.

Column 13, Line 65, delete "monomethactylates," and insert -- monomethacrylates, --, therefor.

Column 14, Line 25, delete "any," and insert -- any --, therefor.

Column 14, Line 42, delete "mega-Pascal's" and insert -- mega-Pascals --, therefor.

Column 15, Line 18, delete "2.4," and insert -- 24, --, therefor.

Column 16, Line 46, delete "amoxicillin," and insert -- amoxicillin, benzylpenicillin, --, therefor.

Column 16, Line 57, delete "ciprofioxacin," and insert -- ciprofloxacin, --, therefor.

Column 18, Line 35, delete ""burst effect" "burst release"" and insert -- "burst effect" or "burst release" --, therefor.

Column 18, Line 65, delete "71," and insert -- 71, 72, --, therefor.

Column 19, Line 14, delete "75% 45" and insert -- 75%, 45 --, therefor.

Column 19, Line 22, delete "75% 45" and insert -- 75%, 45 --, therefor.

Column 19, Line 35, delete "it month," and insert -- 1 month, --, therefor.

Column 20, Line 8, delete "75% 45" and insert -- 75%, 45 --, therefor.

Column 21, Line 37, delete "cyclacillin, methicillin," and insert -- cyclacillin, dicloxacillin, methicillin, --, therefor.

Column 22, Line 20, delete ""burst effect" "burst release"" and insert -- "burst effect" or "burst release" --, therefor.

Column 22, Line 40, delete "110 months," and insert -- 10 months, --, therefor.

Column 22, Lines 54-55, delete "1119, 120 days (4 months), 121, 122, 1123, 124, 125, 1126," and insert -- 119, 120 days (4 months), 121, 122, 123, 124, 125, 126, --, therefor.

Column 22, Line 67, delete "75% 45" and insert -- 75%, 45 --, therefor.

CERTIFICATE OF CORRECTION (continued)
U.S. Pat. No. 10,029,031 B2

Column 23, Line 8, delete "75% 45" and insert -- 75%, 45 --, therefor.

Column 23, Line 61, delete "75% 45" and insert -- 75%, 45 --, therefor.

Column 24, Line 57, delete "about 50 about 50 to 300," and insert -- about 50, about 50 to about 300, --, therefor.

Column 25, Line 44, delete "6:11," and insert -- 6:1, --, therefor.

Column 25, Line 45, delete "11:9," and insert -- 1:9, --, therefor.

Column 26, Line 14, delete "eight" and insert -- weight --, therefor.

Column 29, Line 60, delete "BMP-1, BMP-3, BMP-4, BMP-5, BMP-6," and insert -- BMP-1, BMP-2, BMP-3, BMP-4, BMP-5, BMP-6, BMP-7, --, therefor.

Column 29, Line 66, delete "BMP-4; BMP-6;" and insert -- BMP-4; BMP-5; BMP-6; --, therefor.

Column 30, Line 15, delete "Mowing" and insert -- following --, therefor.

Column 30, Line 25, delete "BCO30959A, AF91389," and insert -- BCO30959, AAF91389, --, therefor.

Column 30, Line 58, delete "nonsteroidal" and insert -- non-steroidal --, therefor.

Column 32, Line 4, delete "hone" and insert -- bone --, therefor.

Column 33, Line 10, delete "tier" and insert -- for --, therefor.

In the Claims

Column 35, Line 26, in Claim 18, delete "filler according" and insert -- filler material according --, therefor.